(12) United States Patent
Kostrzewski

(10) Patent No.: US 9,775,611 B2
(45) Date of Patent: Oct. 3, 2017

(54) CLAM SHELL SURGICAL STAPLING LOADING UNIT

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 339 days.

(21) Appl. No.: 14/590,059

(22) Filed: Jan. 6, 2015

(65) Prior Publication Data
US 2016/0192927 A1 Jul. 7, 2016

(51) Int. Cl.
| | | |
|---|---|---|
| *A61B 17/10* | (2006.01) | |
| *A61B 17/072* | (2006.01) | |
| *A61B 17/064* | (2006.01) | |
| *A61B 17/29* | (2006.01) | |
| *A61B 17/42* | (2006.01) | |
| *A61B 90/00* | (2016.01) | |

(52) U.S. Cl.
CPC .... *A61B 17/07207* (2013.01); *A61B 17/0643* (2013.01); *A61B 2017/07214* (2013.01); *A61B 2017/07278* (2013.01); *A61B 2017/2927* (2013.01); *A61B 2017/2937* (2013.01); *A61B 2017/4216* (2013.01); *A61B 2090/038* (2016.02)

(58) Field of Classification Search
CPC .............. A61B 17/0643; A61B 17/072; A61B 17/07207; A61B 2017/07278; A61B 2017/07214; A61B 2017/2927; A61B 2017/2945; A61B 2017/2947; A61B 17/28; A61B 17/2804; A61B 17/2812; A61B 17/2816; A61B 17/282; A61B 2017/2808; A61B 2017/2926

USPC ................. 606/142, 205, 207, 219
See application file for complete search history.

(56) References Cited

U.S. PATENT DOCUMENTS

| | | |
|---|---|---|
| 2,891,250 A | 6/1959 | Hirata |
| 3,080,564 A | 3/1963 | Strekopitov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |

(Continued)

OTHER PUBLICATIONS

U.S. Appl. No. 14/638,482, filed Mar. 4, 2015, inventor: Kostrzewski.

(Continued)

*Primary Examiner* — Diane Yabut
*Assistant Examiner* — Martin T Ton

(57) ABSTRACT

A clamshell stapling end effector includes first and second jaws and defines an end effector axis. The first jaw has proximal, central, and distal portions. The central portion includes a first tissue contacting surface and defines a cavity. The second jaw includes a second tissue contacting surface and is rotatably secured to the first jaw about a rotation axis. The rotation axis is parallel to the end effector axis. The second jaw has a folded position such that the second jaw is positioned within the cavity of the first jaw with the first and second tissue contacting surfaces parallel to one another and facing in the same direction and a clamped position such that the first and second tissue contacting surfaces oppose one another.

19 Claims, 25 Drawing Sheets

(56) References Cited

U.S. PATENT DOCUMENTS

| | | | |
|---|---|---|---|
| 3,795,034 A | 3/1974 | Strekopytov et al. | |
| 3,822,818 A | 7/1974 | Strekopytov et al. | |
| 3,935,981 A | 2/1976 | Akopov et al. | |
| 3,949,923 A | 4/1976 | Akopov et al. | |
| 4,047,654 A | 9/1977 | Alvarado | |
| 4,077,121 A * | 3/1978 | Waller | A47J 43/26 30/120.3 |
| 4,216,891 A | 8/1980 | Behlke | |
| 4,244,372 A | 1/1981 | Kapitanov et al. | |
| 4,296,881 A | 10/1981 | Lee | |
| 4,305,539 A | 12/1981 | Korolkov et al. | |
| 4,354,628 A | 10/1982 | Green | |
| 4,378,901 A | 4/1983 | Akopov et al. | |
| 4,383,634 A | 5/1983 | Green | |
| 4,402,444 A | 9/1983 | Green | |
| 4,415,112 A | 11/1983 | Green | |
| D273,513 S | 4/1984 | Spreckelmeier | |
| 4,442,964 A | 4/1984 | Becht | |
| 4,470,533 A | 9/1984 | Schuler | |
| 4,475,679 A | 10/1984 | Fleury, Jr. | |
| 4,485,811 A | 12/1984 | Chernousov et al. | |
| 4,506,670 A | 3/1985 | Crossley | |
| 4,506,671 A | 3/1985 | Green | |
| 4,508,253 A | 4/1985 | Green | |
| 4,522,327 A | 6/1985 | Korthoff et al. | |
| 4,527,724 A | 7/1985 | Chow et al. | |
| 4,530,453 A | 7/1985 | Green | |
| 4,550,870 A | 11/1985 | Krumme et al. | |
| 4,566,620 A | 1/1986 | Green et al. | |
| 4,568,009 A | 2/1986 | Green | |
| 4,573,622 A | 3/1986 | Green et al. | |
| 4,580,712 A | 4/1986 | Green | |
| 4,585,153 A | 4/1986 | Failla et al. | |
| 4,589,582 A | 5/1986 | Bilotti | |
| 4,602,634 A | 7/1986 | Barkley | |
| 4,605,001 A | 8/1986 | Rothfuss et al. | |
| 4,605,004 A | 8/1986 | Di Giovanni et al. | |
| 4,606,344 A | 8/1986 | Di Giovanni | |
| 4,606,345 A | 8/1986 | Dorband et al. | |
| 4,607,636 A | 8/1986 | Kula et al. | |
| 4,612,933 A | 9/1986 | Brinkerhoff et al. | |
| 4,617,928 A | 10/1986 | Alfranca | |
| 4,632,290 A | 12/1986 | Green et al. | |
| 4,665,916 A | 5/1987 | Green | |
| 4,684,051 A | 8/1987 | Akopov et al. | |
| 4,714,187 A | 12/1987 | Green | |
| 4,715,520 A | 12/1987 | Roehr, Jr. et al. | |
| 4,728,020 A | 3/1988 | Green et al. | |
| 4,767,044 A | 8/1988 | Green | |
| 4,788,978 A | 12/1988 | Strekopytov et al. | |
| 4,802,614 A | 2/1989 | Green et al. | |
| 4,805,823 A | 2/1989 | Rothfuss | |
| 4,819,853 A | 4/1989 | Green | |
| 4,848,637 A | 7/1989 | Pruitt | |
| 4,869,414 A | 9/1989 | Green et al. | |
| 4,881,544 A | 11/1989 | Green et al. | |
| 4,881,545 A | 11/1989 | Isaacs et al. | |
| 4,915,100 A | 4/1990 | Green | |
| 4,930,503 A | 6/1990 | Pruitt | |
| 4,938,408 A | 7/1990 | Bedi et al. | |
| 4,941,623 A | 7/1990 | Pruitt | |
| 4,951,861 A | 8/1990 | Schulze et al. | |
| 4,964,559 A | 10/1990 | Deniega et al. | |
| 5,005,754 A | 4/1991 | Van Overloop | |
| 5,018,657 A | 5/1991 | Pedlick et al. | |
| 5,071,052 A | 12/1991 | Rodak et al. | |
| 5,100,042 A | 3/1992 | Gravener et al. | |
| 5,116,349 A | 5/1992 | Aranyi | |
| 5,137,198 A | 8/1992 | Nobis et al. | |
| 5,172,845 A | 12/1992 | Tejeiro | |
| 5,190,203 A | 3/1993 | Rodak | |
| 5,219,111 A | 6/1993 | Bilotti et al. | |
| 5,240,163 A | 8/1993 | Stein et al. | |
| 5,344,060 A | 9/1994 | Gravener et al. | |
| 5,368,599 A | 11/1994 | Hirsch et al. | |
| 5,405,073 A | 4/1995 | Porter | |
| 5,413,267 A | 5/1995 | Solyntjes et al. | |
| 5,439,155 A | 8/1995 | Viola | |
| 5,452,836 A | 9/1995 | Huitema et al. | |
| 5,458,279 A | 10/1995 | Plyley | |
| 5,462,215 A | 10/1995 | Viola et al. | |
| 5,464,144 A | 11/1995 | Guy et al. | |
| 5,465,894 A | 11/1995 | Clark et al. | |
| 5,470,006 A | 11/1995 | Rodak | |
| 5,470,008 A | 11/1995 | Rodak | |
| 5,470,009 A | 11/1995 | Rodak | |
| 5,497,934 A | 3/1996 | Brady et al. | |
| 5,503,320 A | 4/1996 | Webster et al. | |
| 5,507,773 A | 4/1996 | Huitema et al. | |
| 5,509,596 A | 4/1996 | Green et al. | |
| 5,542,594 A | 8/1996 | McKean et al. | |
| 5,547,117 A | 8/1996 | Hamblin et al. | |
| 5,558,266 A | 9/1996 | Green et al. | |
| 5,579,978 A * | 12/1996 | Green | A61B 17/072 227/175.3 |
| 5,580,067 A | 12/1996 | Hamblin et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,615,820 A | 4/1997 | Viola | |
| 5,641,111 A | 6/1997 | Ahrens et al. | |
| 5,678,748 A | 10/1997 | Plyley et al. | |
| 5,697,543 A | 12/1997 | Burdorff | |
| 5,706,997 A | 1/1998 | Green et al. | |
| 5,706,998 A | 1/1998 | Plyley et al. | |
| 5,725,536 A * | 3/1998 | Oberlin | A61B 17/07207 606/139 |
| 5,732,871 A | 3/1998 | Clark et al. | |
| 5,735,445 A | 4/1998 | Vidal et al. | |
| 5,794,834 A | 8/1998 | Hamblin et al. | |
| 5,810,240 A | 9/1998 | Robertson | |
| 5,855,311 A | 1/1999 | Hamblin et al. | |
| 5,878,937 A | 3/1999 | Green et al. | |
| 5,893,506 A | 4/1999 | Powell | |
| 5,894,979 A | 4/1999 | Powell | |
| 5,964,394 A | 10/1999 | Robertson | |
| 6,045,560 A | 4/2000 | McKean et al. | |
| 6,302,311 B1 | 10/2001 | Adams et al. | |
| 6,638,285 B2 | 10/2003 | Gabbay | |
| 6,805,273 B2 | 10/2004 | Bilotti et al. | |
| 6,817,508 B1 | 11/2004 | Racenet et al. | |
| 6,988,650 B2 | 1/2006 | Schwemberger et al. | |
| 7,070,083 B2 | 7/2006 | Jankowski | |
| 7,134,587 B2 | 11/2006 | Schwemberger et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,210,609 B2 | 5/2007 | Leiboff et | |
| 7,235,089 B1 | 6/2007 | McGuckin, Jr. | |
| 7,237,708 B1 | 7/2007 | Guy et al. | |
| 7,275,674 B2 | 10/2007 | Racenet et al. | |
| RE40,237 E | 4/2008 | Bilotti et al. | |
| 7,407,076 B2 | 8/2008 | Racenet et al. | |
| 7,431,190 B2 | 10/2008 | Hoffman | |
| 7,510,107 B2 | 3/2009 | Timm et al. | |
| 7,522,854 B2 | 4/2009 | Kinouchi et al. | |
| 7,549,563 B2 | 6/2009 | Mather et al. | |
| 7,568,605 B2 | 8/2009 | Kruszynski | |
| 7,641,092 B2 | 1/2010 | Kruszynski et al. | |
| 7,717,312 B2 | 5/2010 | Beetel | |
| 7,731,073 B2 | 6/2010 | Wixey et al. | |
| 7,735,704 B2 | 6/2010 | Bilotti | |
| 7,766,207 B2 | 8/2010 | Mather et al. | |
| 7,810,690 B2 | 10/2010 | Bilotti et al. | |
| 8,016,176 B2 | 9/2011 | Kasvikis et al. | |
| 8,033,439 B2 | 10/2011 | Racenet et al. | |
| 8,231,041 B2 | 7/2012 | Marczyk et al. | |
| 8,424,738 B2 | 4/2013 | Kasvikis | |
| 8,499,994 B2 | 8/2013 | D'Arcangelo | |
| 8,623,044 B2 | 1/2014 | Timm et al. | |
| 8,757,467 B2 | 6/2014 | Racenet et al. | |
| 8,789,737 B2 | 7/2014 | Hodgkinson et al. | |

(56) References Cited

U.S. PATENT DOCUMENTS

| | | |
|---|---|---|
| 2004/0164123 A1 | 8/2004 | Racenet et al. |
| 2005/0247752 A1 | 11/2005 | Kelly et al. |
| 2005/0247753 A1 | 11/2005 | Kelly et al. |
| 2006/0151568 A1 | 7/2006 | Weller et al. |
| 2006/0163312 A1 | 7/2006 | Viola et al. |
| 2007/0167960 A1* | 7/2007 | Roth ................ A61B 17/0218 606/153 |
| 2007/0187456 A1 | 8/2007 | Viola et al. |
| 2009/0277948 A1 | 11/2009 | Beardsley et al. |
| 2010/0048988 A1 | 2/2010 | Pastorelli et al. |
| 2012/0253329 A1 | 10/2012 | Zemlok et al. |
| 2013/0105554 A1 | 5/2013 | Kostrzewski |
| 2013/0256374 A1* | 10/2013 | Shelton, IV ..... A61B 17/07292 227/176.1 |

OTHER PUBLICATIONS

Extended European Search Report for EP 16 150 128.3 dated Jun. 10, 2016.

\* cited by examiner

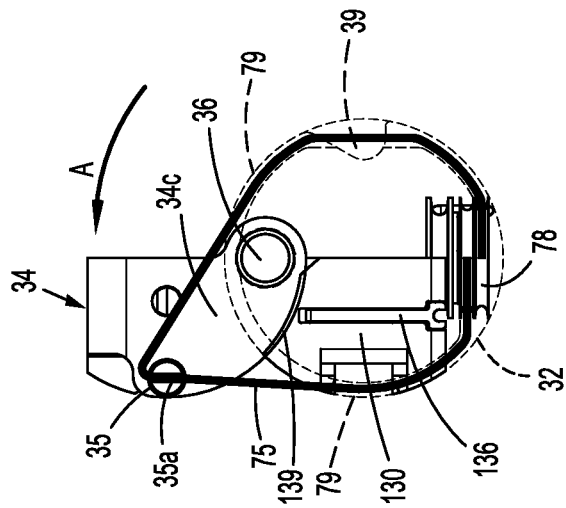
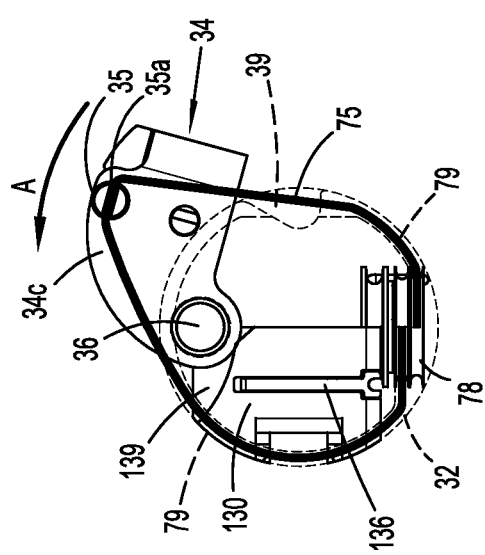
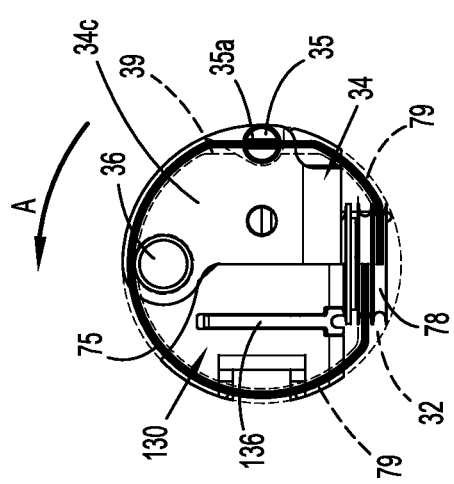

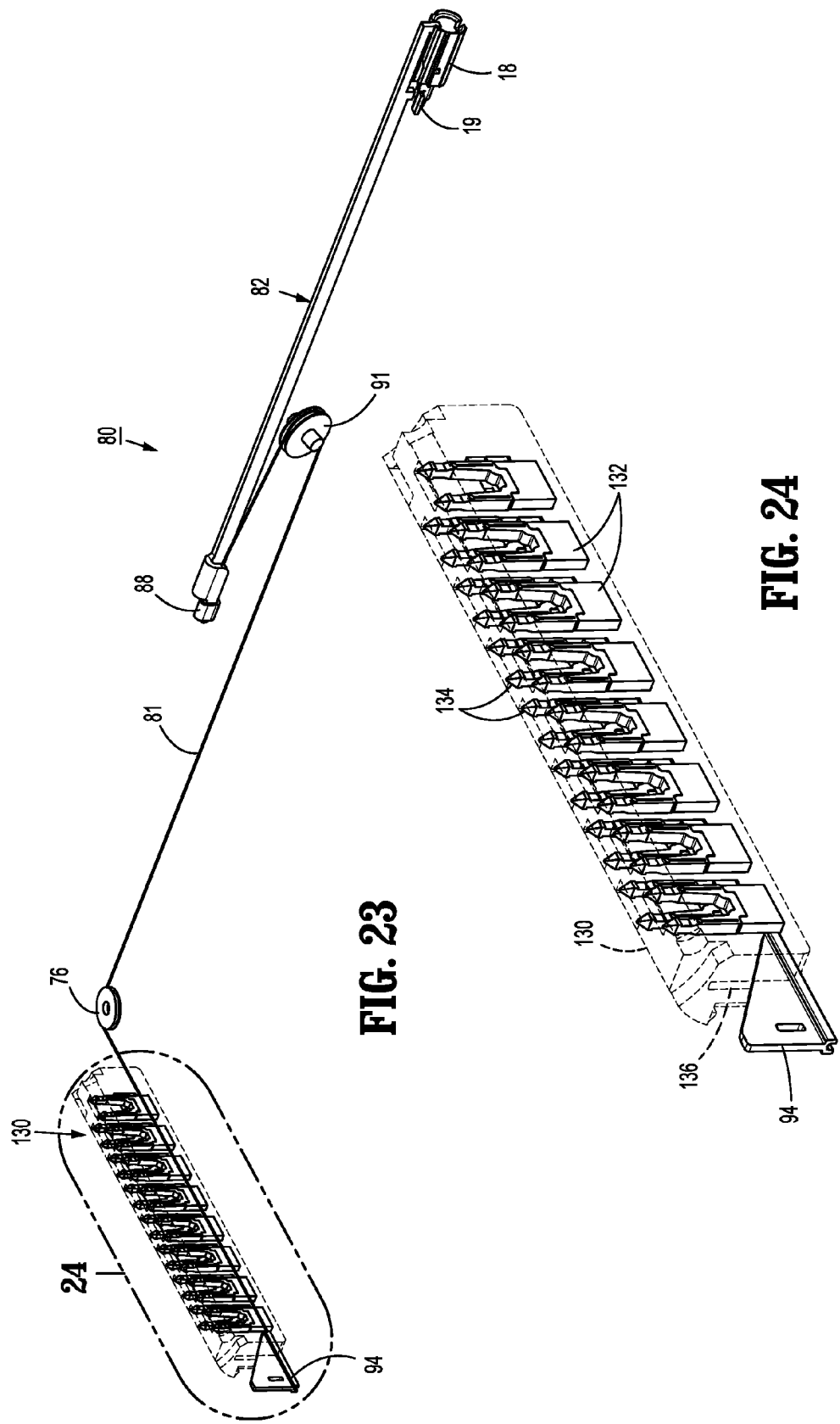

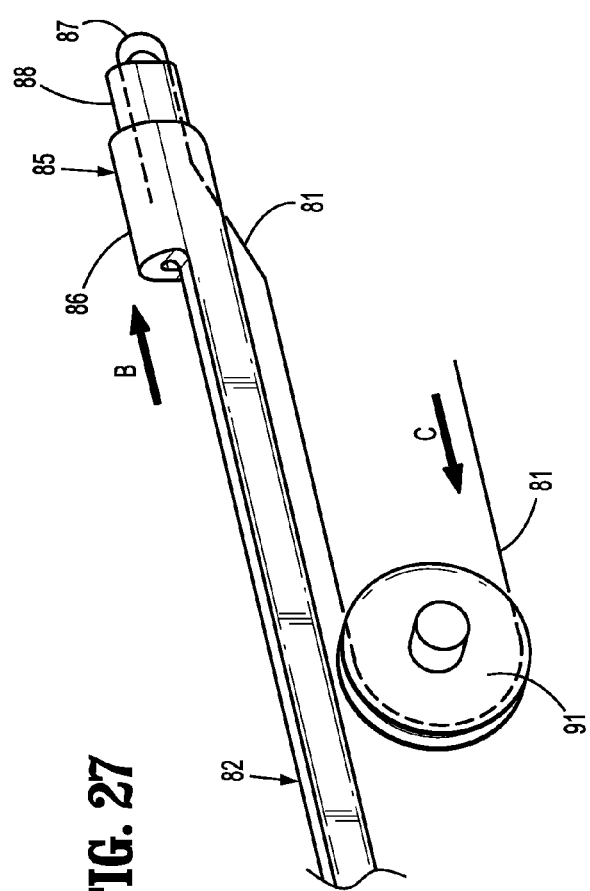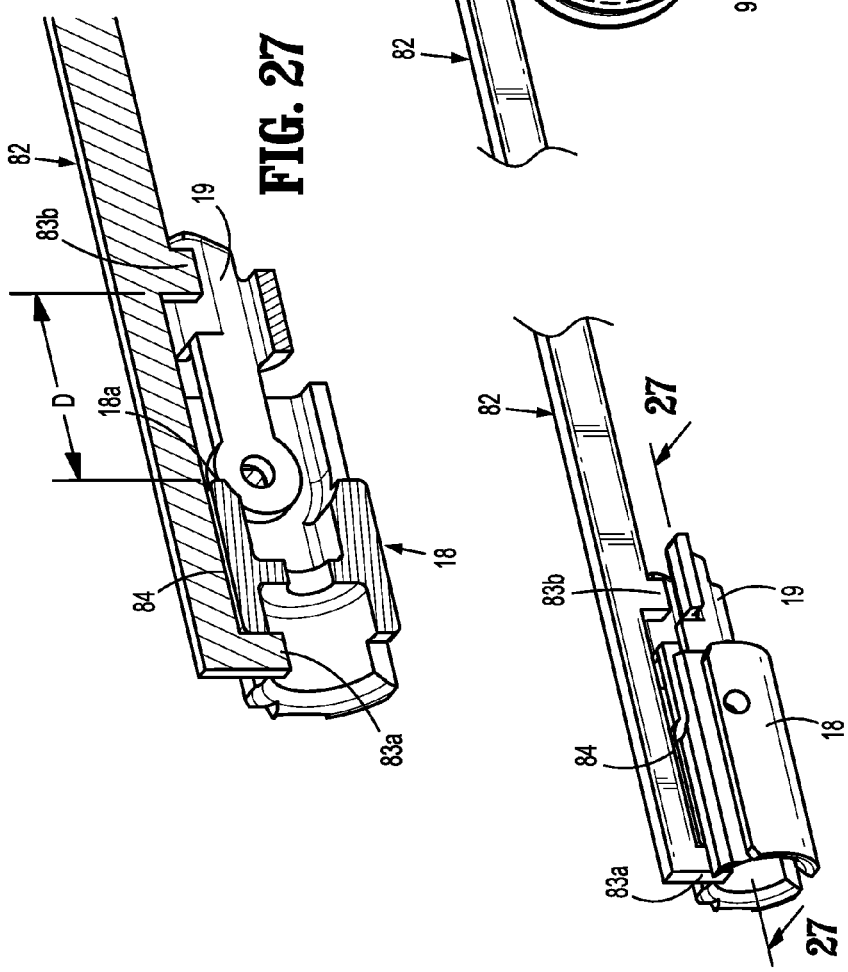

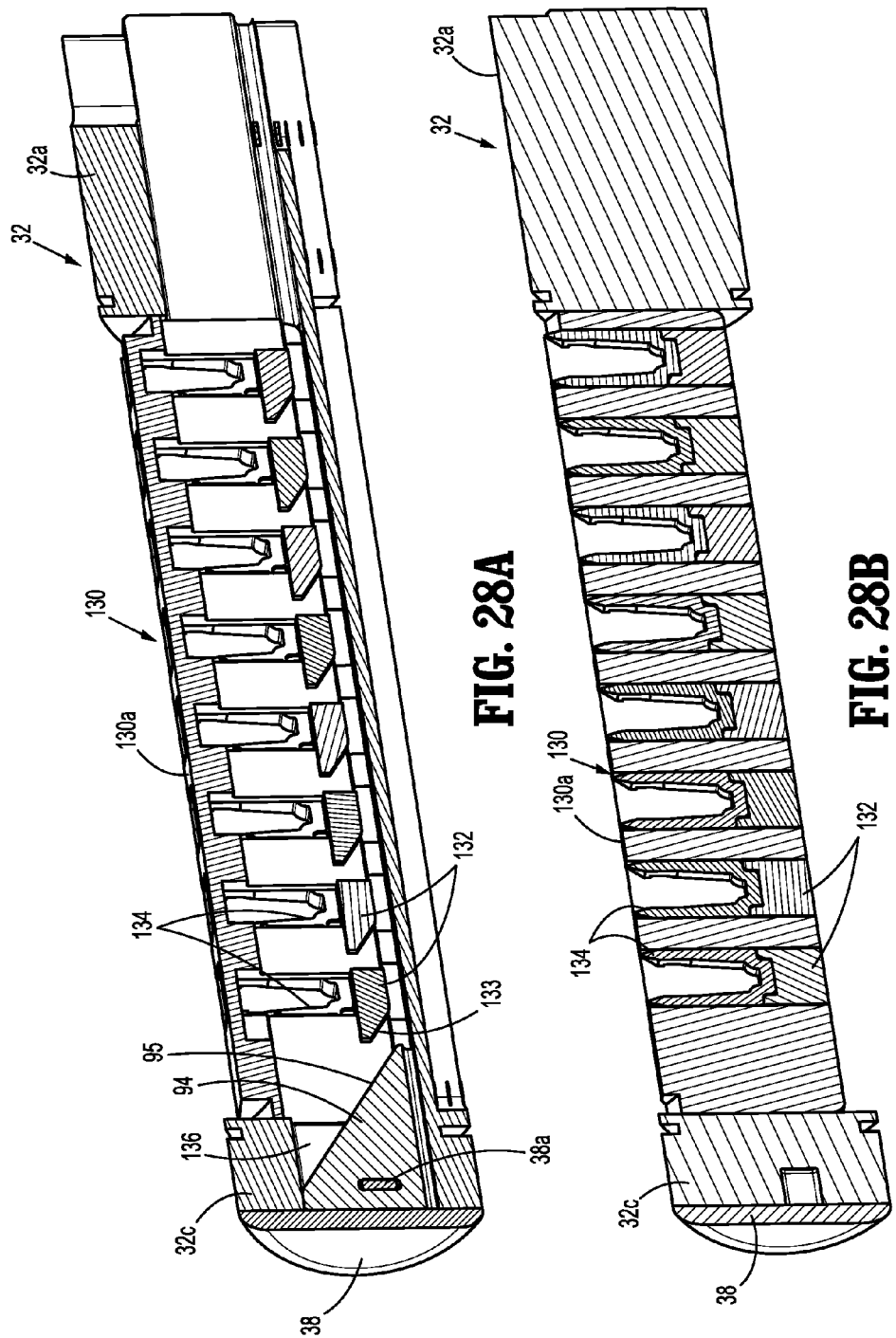

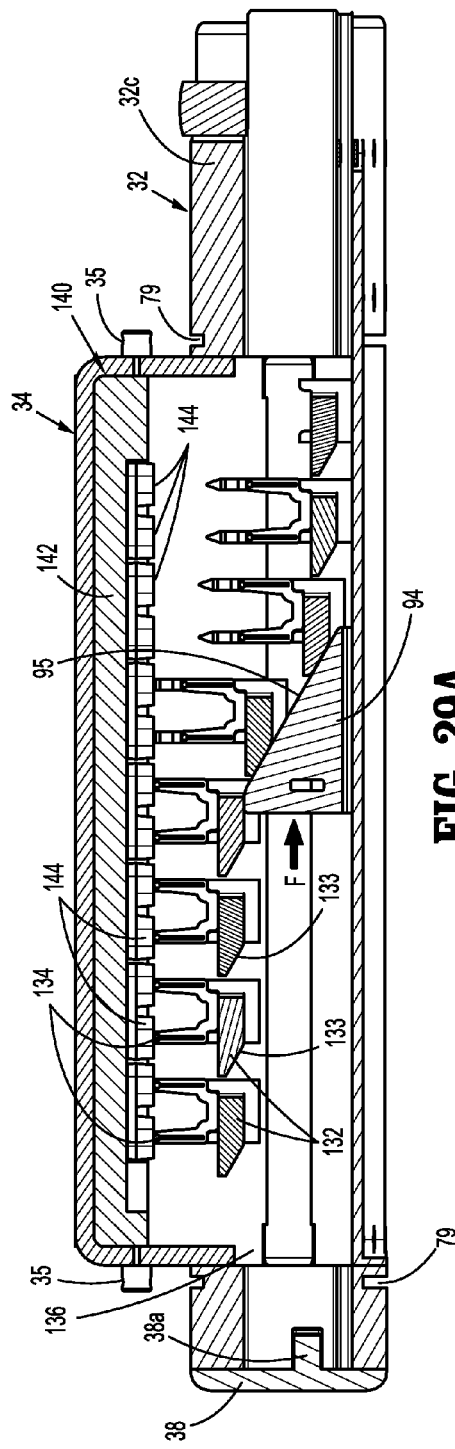
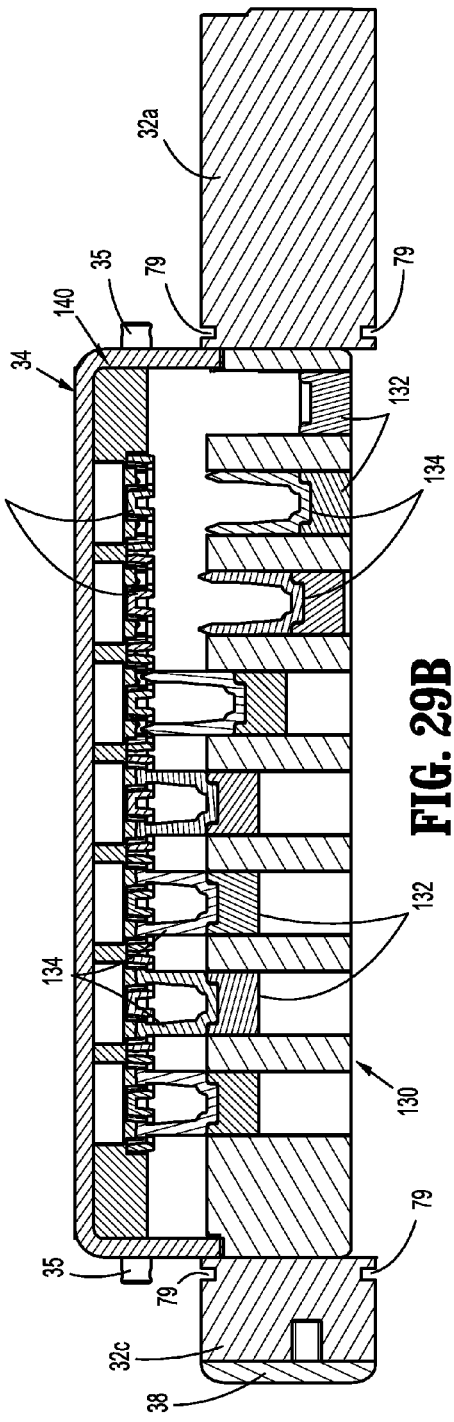
FIG. 29A
FIG. 29B

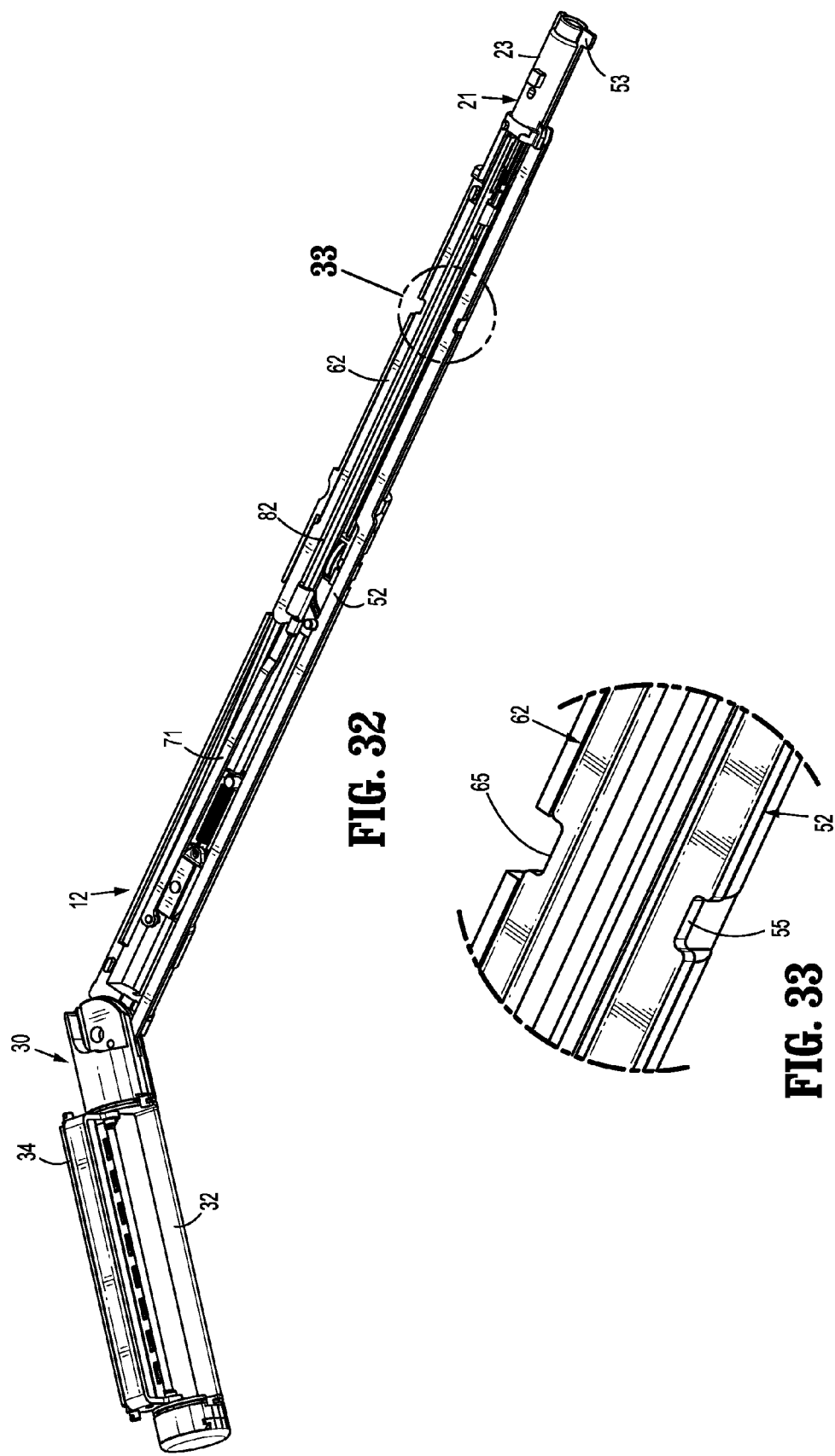

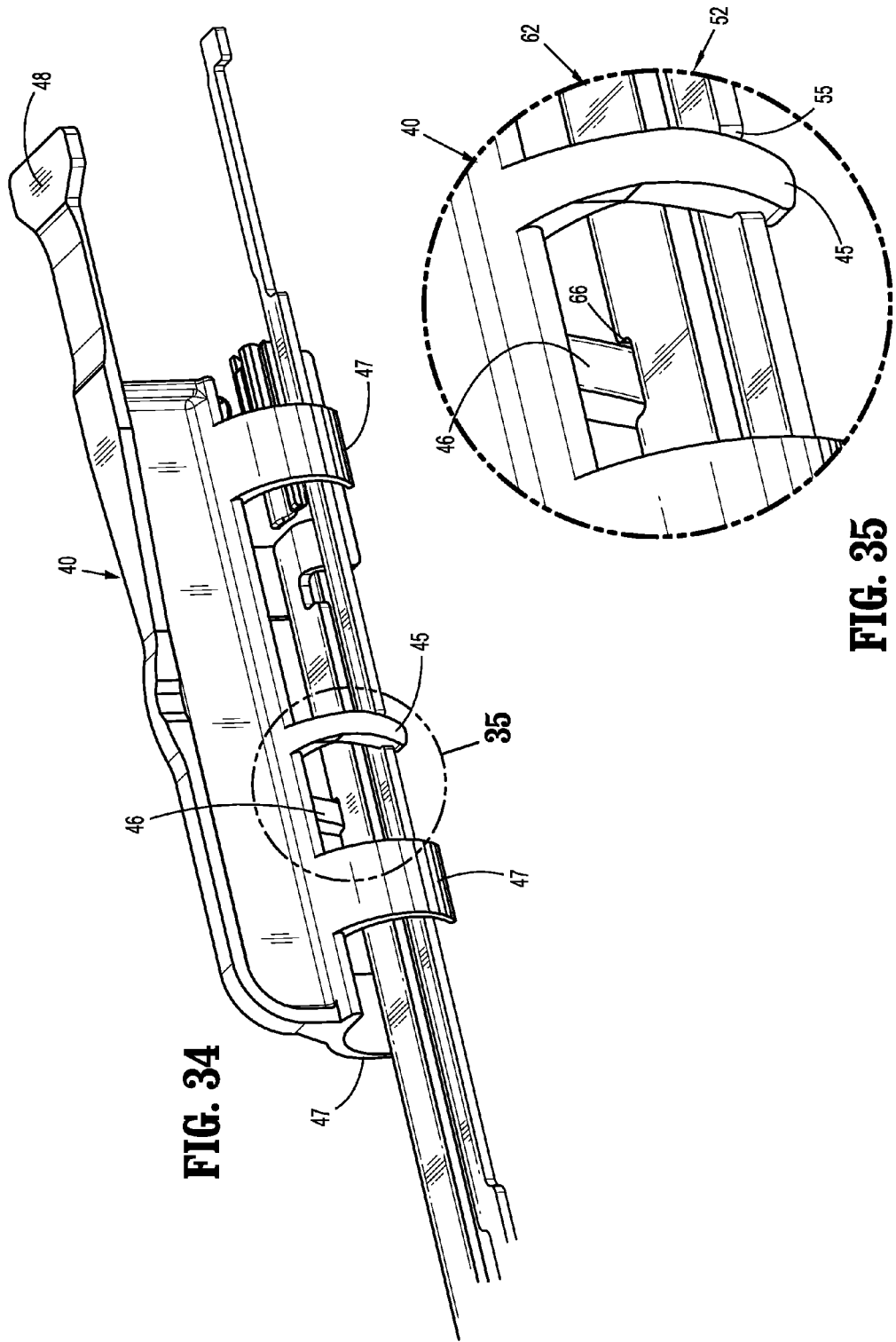

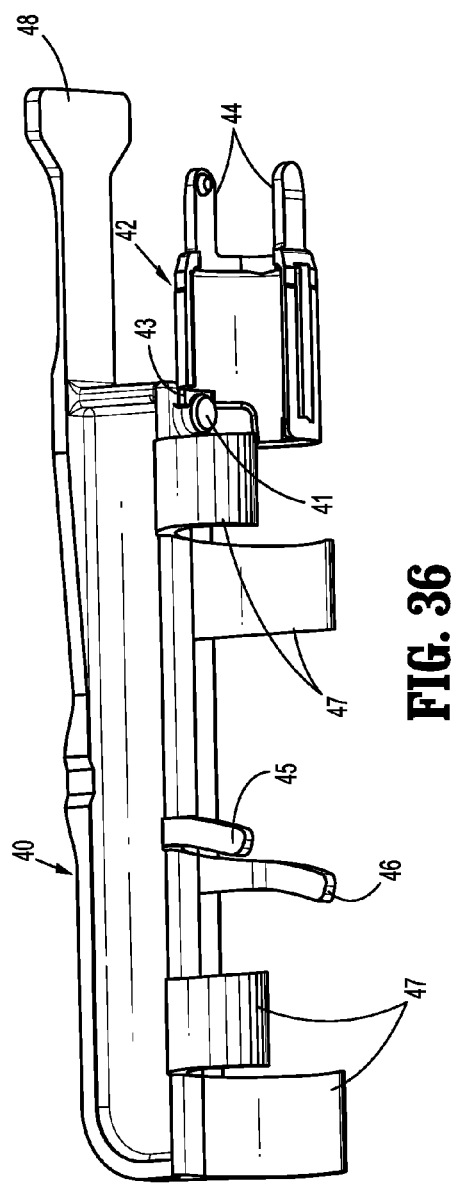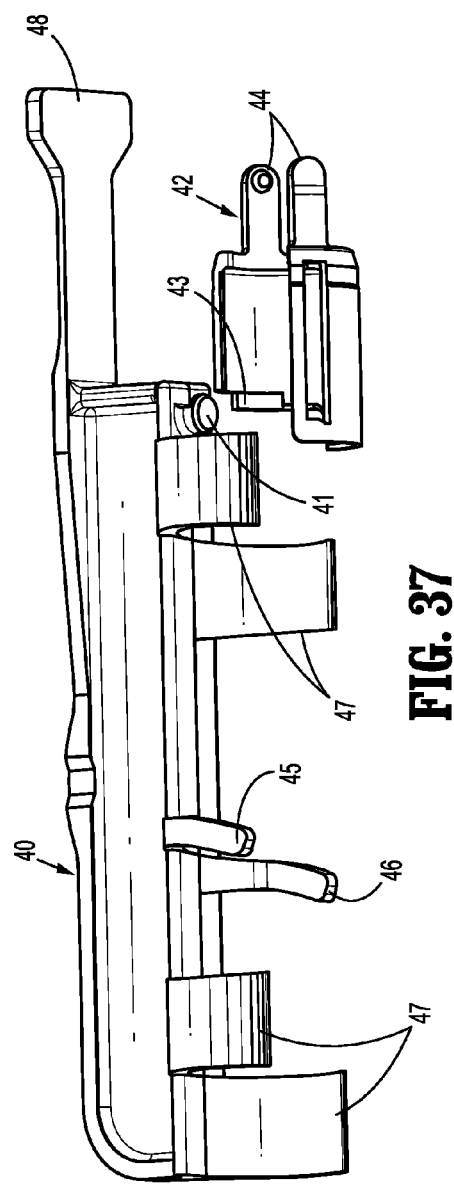

CLAM SHELL SURGICAL STAPLING LOADING UNIT

BACKGROUND

1. Technical Field

The present disclosure relates to surgical instruments and, more specifically, to instruments for closing the open end of a hollow organ.

2. Discussion of Related Art

During hysterectomy procedures, such as total laparoscopic hysterectomy (TLH) procedures, the uterus and cervix are removed, creating an approximately circular structure at end of the vaginal canal called the vaginal cuff. The closure of the remaining vaginal cuff can be one of the most challenging aspects of the procedure. It is also considered to be one of the barriers to adoption of laparoscopic surgery to those trained in open procedures.

After the uterus is removed it is necessary to close the vaginal cuff while avoiding dehiscence, which is when a wound ruptures along a surgical suture. Currently the vaginal cuff closure is done manually by suturing the cuff with needle and suture or with a stitching surgical instrument. Both methods require a good deal of surgical skill and time.

There is a need for an instrument that can close a vaginal cuff that requires less skill, saves time, and provides strong, consistent anastomosis.

SUMMARY

In an aspect of the present disclosure, an end effector includes first and second jaws. The first jaw has proximal, central, and distal portions and defines an end effector axis. The central portion has a first tissue contacting surface and defines a cavity. The second jaw has a second tissue contacting surface and is rotatably secured to the first jaw about a rotation axis which is parallel to the end effector axis. The second jaw has a folded position such that the second jaw is positioned within the cavity of the first jaw with the second tissue contacting surface of the second jaw facing in the same direction as the first tissue contacting surface of the first jaw. The second jaw is rotatable to a clamped position such that the second jaw is rotated about the rotation axis with the second tissue contacting surface of the second jaw in opposition to the first tissue contacting surface of the first jaw.

In aspects, the first jaw includes a fastener cartridge that has a plurality of fasteners. The first jaw may include a sled that is translatable through the fastener cartridge to eject the plurality of fasteners from the first jaw towards the second jaw when the second jaw is in the clamped position.

In some aspects, the second jaw includes a proximal flange, a distal flange, and a central portion that connects the proximal and distal flanges. The proximal and distal portions of the first jaw may each define a folded stop recess adjacent the cavity. Each of the proximal and distal flanges of the second jaw may include a stop pin that extends away from the central portion of the second jaw. The stop pins may be received within the folded stop recesses when the second jaw is in the folded position.

In another aspect of the present disclosure, a loading unit includes a housing, an end effector, a clamping mechanism, and a firing mechanism. The housing defines a longitudinal axis and includes a connector positioned at a proximal end of the housing. The connector is configured to couple the loading unit to a surgical instrument. The end effector is supported at a distal end of the housing and includes first and second jaws. The first jaw has proximal, central, and distal portions and defines and end effector axis. The central portion has a first tissue contacting surface and defines a cavity. The central portion includes a plurality of fasteners. The second jaw has a second tissue contacting surface and is rotatably secured to the first jaw about a rotation axis which is parallel to the end effector axis. The second jaw has a folded position such that the second jaw is positioned within the cavity of the first jaw with the second tissue contacting surface of the second jaw facing the same direction as the first tissue contacting surface of the first jaw. The second jaw is rotatable to a clamped position such that the second jaw is rotated about the rotation axis with the second tissue contacting surface of the second jaw in opposition to the first tissue contacting surface of the first jaw. The clamping mechanism is disposed within the housing and is operatively associated with the second jaw to rotate the second jaw between the folded and clamped positions. The clamping mechanism includes a clamping rod, a clamping shaft, and a pivot arm positioned between the clamping rod and the clamping shaft to longitudinally translate the clamping rod in response to longitudinal translation of the clamping shaft. The firing mechanism is disposed within the housing and is operatively associated with the first jaw to eject the plurality of fasteners from the first jaw towards the second jaw when the second jaw is in the clamped position. The firing mechanism includes a fire rod that is longitudinally translatable within the housing.

In aspects, the distal end of the clamping shaft includes a clamping hook and the pivot arm includes a first end that is rotatably coupled to the housing and a second end that is coupled to a proximal end of the clamping rod. The pivot arm may include a cam follower positioned between its first and second ends. The clamping hook may engage the cam follower of the pivot arm to rotate the pivot arm between folded and clamped positions. Rotation of the pivot arm between the folded and clamped positions effects translation of the clamping rod.

In some aspects, the clamping rod is coupled to a clamping cable which is also coupled to the second jaw. The clamping cable rotates the second jaw between the folded and clamped positions. Distal translation of the clamping rod may tension the clamping cable to rotate the second jaw towards the clamped position and proximal translation of the clamping rod may tension the clamping cable to rotate the second jaw towards the folded position.

In certain aspects, the clamping mechanism includes a cable tensioner. A first portion of the clamping cable may pass form the clamping rod, through the cable tensioner, and into the end effector. The cable tensioner may be biased proximally to apply tension to the first portion of the clamping cable.

In particular aspects, the end effector includes idler, proximal, and distal pulleys rotatably attached to a lower surface of the end effector. The idler pulley may be positioned adjacent a proximal end of the end effector. The distal pulley may be positioned adjacent a distal end of the end effector. The proximal pulley is positioned between the idler and distal pulleys. Each of the proximal and distal portions of the first jaw of the end effector defines a groove adjacent a central portion. A second portion of the clamping cable may pass around the idler pulley, the proximal pulley, the distal pulley, and into the groove defined in the distal portion of the first jaw. The second portion of the clamping cable is coupled to the second jaw.

In aspects, a distal end of the fire rod is coupled to a firing cable which is coupled to a sled disposed within the first jaw.

The sled may be slidable through the first jaw to eject the plurality of fasteners from the first jaw. The sled may be proximally slidable parallel to the end effector axis to eject the plurality of fasteners from the first jaw. Distal translation of the fire rod may slide the sled proximally.

In some aspects, the loading unit includes an articulation mechanism. The articulation mechanism may include an articulation rod that is disposed within the housing and extends from an articulation flag positioned within the connector of the housing to a distal end that is coupled to the end effector. The articulation flag may be longitudinally translatable to articulate the end effector relative to the housing. The end effector may be articulable between straight and articulated configurations. In the straight configuration the end effector axis is articulated a first angle relative to the longitudinal axis of the housing. In the articulated configuration the end effector axis may be articulated a second angle relative to the longitudinal axis of the housing. The first angle may be different from the second angle. The second angle may be in the range of about −4° to about 100°.

In another aspect of the present disclosure, a method for closing a vaginal cuff includes inserting a loading unit through an opening in a straight configuration, articulating an end effector of the loading unit such that an end effector axis of the end effector is perpendicular to a vaginal cuff of a patient, rotating a second jaw of the end effector for a folded position to a clamped position, and ejecting a plurality of fasteners from a first jaw of the end effector towards the second jaw to close the vaginal cuff. In the straight configuration of the loading unit, the end effector axis of the end effector is aligned with a longitudinal axis defined by a housing of the loading unit. The end effector is supported on a distal end of the housing. During insertion of the loading unit, the second jaw is in a folded position relative to the first jaw. When the second jaw is rotated to the clamped position, the vaginal cuff is positioned between tissue contacting surfaces of the first and second jaws.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 20 is an end view of the end effector of FIG. 3 with the end cap removed and the retainer jaw in a folded position;

FIG. 21 is an end view of the end effector of FIG. 3 with the end cap removed and the retainer jaw in an open position;

FIG. 22 is an end view of the end effector of FIG. 3 with the end cap removed and the retainer jaw in a clamped position;

FIG. 23 is a perspective view of the firing mechanism of the loading unit of FIG. 1;

FIG. 24 is an enlarged view of the indicated area of detail of FIG. 23;

FIG. 25 is a perspective view of a proximal portion of the firing shaft of FIG. 23;

FIG. 26 is a perspective view of a distal portion of the firing shaft and the firing pulley of FIG. 23;

FIG. 27 is a cross-sectional view taken along the section line 27-27 of FIG. 25;

FIG. 28A is a cross-sectional view taken along the section line 28A-28A of FIG. 5 with a sled in an initial position;

FIG. 28B is a cross-sectional view taken along the section line 28B-28B of FIG. 5 with fasteners disposed within the fastener cartridge;

FIG. 29A is a cross-sectional view of the end effector of FIG. 28A with the sled partially pulled through the fastener cartridge and including the retainer jaw in the clamped position;

FIG. 29B is a cross-sectional view of the end effector of FIG. 28B with the sled partially pulled through the fastener cartridge to eject fasteners from the fastener cartridge and including the retainer jaw in the clamped position;

FIG. 32 is a perspective view of the loading unit of FIG. 1 in a shipping configuration with the upper housing portion removed;

FIG. 33 is an enlarged view of the indicated area of detail of FIG. 32;

FIG. 34 is a perspective view of a proximal portion of the loading unit of FIG. 32 with the lower housing portion removed;

FIG. 35 is an enlarged view of the indicated area of detail of FIG. 34;

FIG. 36 is a perspective view of the shipping wedge and locking ring of FIG. 1;

FIG. 37 is a perspective view of the shipping wedge and the locking ring of FIG. 36 with the locking ring rotated to an unlocked position;

DETAILED DESCRIPTION

Figure 1:
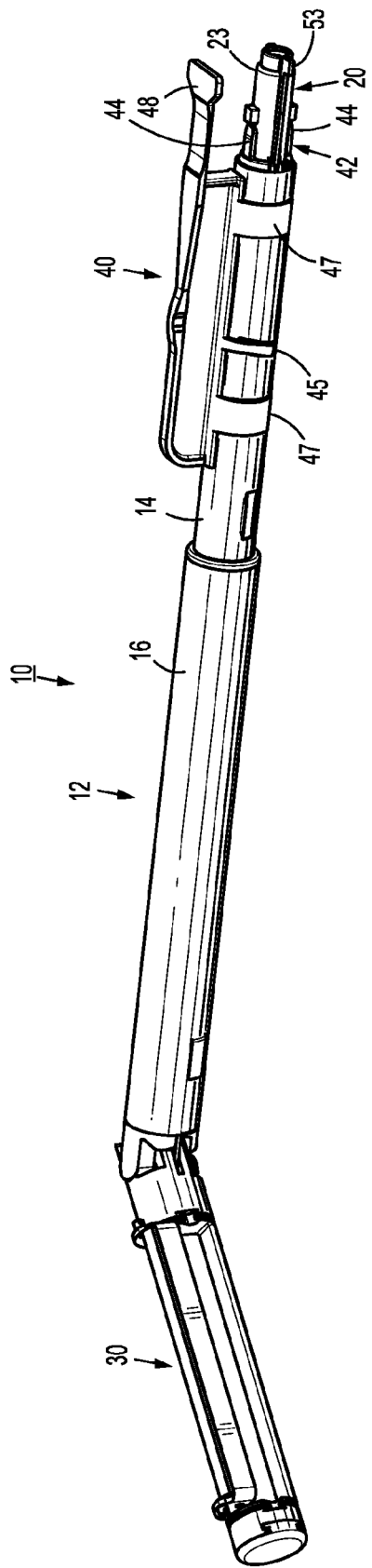
FIG. 1 is a perspective view of a loading unit provided in accordance with the present disclosure in a shipping configuration.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates to a loading unit for a powered or manual surgical handle for including an end effector for joining tissue. The end effector has jaws that rotate to a closed position and can be in the form of a clam shell. The end effector includes a retainer jaw that is pivotally received in a recess defined by a fastener jaw. The retainer jaw is pivoted from the recess to a clamped position and then fasteners are ejected from the fastening cartridge towards the retainer cartridge to secure tissue captured between the fastener and retainer jaws. As detailed below, the loading unit may be used to during a total laparoscopic hysterectomy to close a vaginal cuff.

Referring now to FIG. 1, the loading unit 10 is provided in accordance with the present disclosure and includes an elongated body 12 extending from a connector 23 to an end effector 30. As shown in FIG. 1 and discussed in greater detail below, the loading unit 10 is in a shipping configuration with a shipping wedge 40 secured about a proximal tube 14 of the elongated body 12. The connector 23 is configured to couple the loading unit 10 to a surgical instrument (not shown) including a drive rod which actuates the loading unit 10 to articulate the end effector 30 relative to the elongated body 12, to clamp tissue within the end effector 30, and to form fasteners through the clamped tissue.

The connector 23 of the loading unit 10 may be configured for selective connection to a powered hand held electromechanical instrument (not shown), may be configured for selective connection to an adapter for a powered or manual instrument, or may be configured for selective connection to a manually actuated handle assembly. For a detailed description of the structure and function of an exemplary manually actuated handle assembly, please refer to commonly owned U.S. Pat. No. 8,789,737. For a detailed description of the structure and function of an exemplary electromechanical instrument and adapter, please refer to commonly owned U.S. patent application Ser. No. 13/484,975, filed on May 31, 2012, now published as U.S. Patent Publication No. 2012/0253329. Each of these disclosures is incorporated herein by reference in its entirety.

Any of the embodiments disclosed herein can include microchips or other devices for identification purposes, for measuring certain parameters, etc. The entire disclosures of the following application are hereby incorporated by reference herein: U.S. provisional No. 62/017,626, filed Jun. 26, 2014, and U.S. application Ser. No. 14/172,109, filed Feb. 4, 2014.

Figure 2:
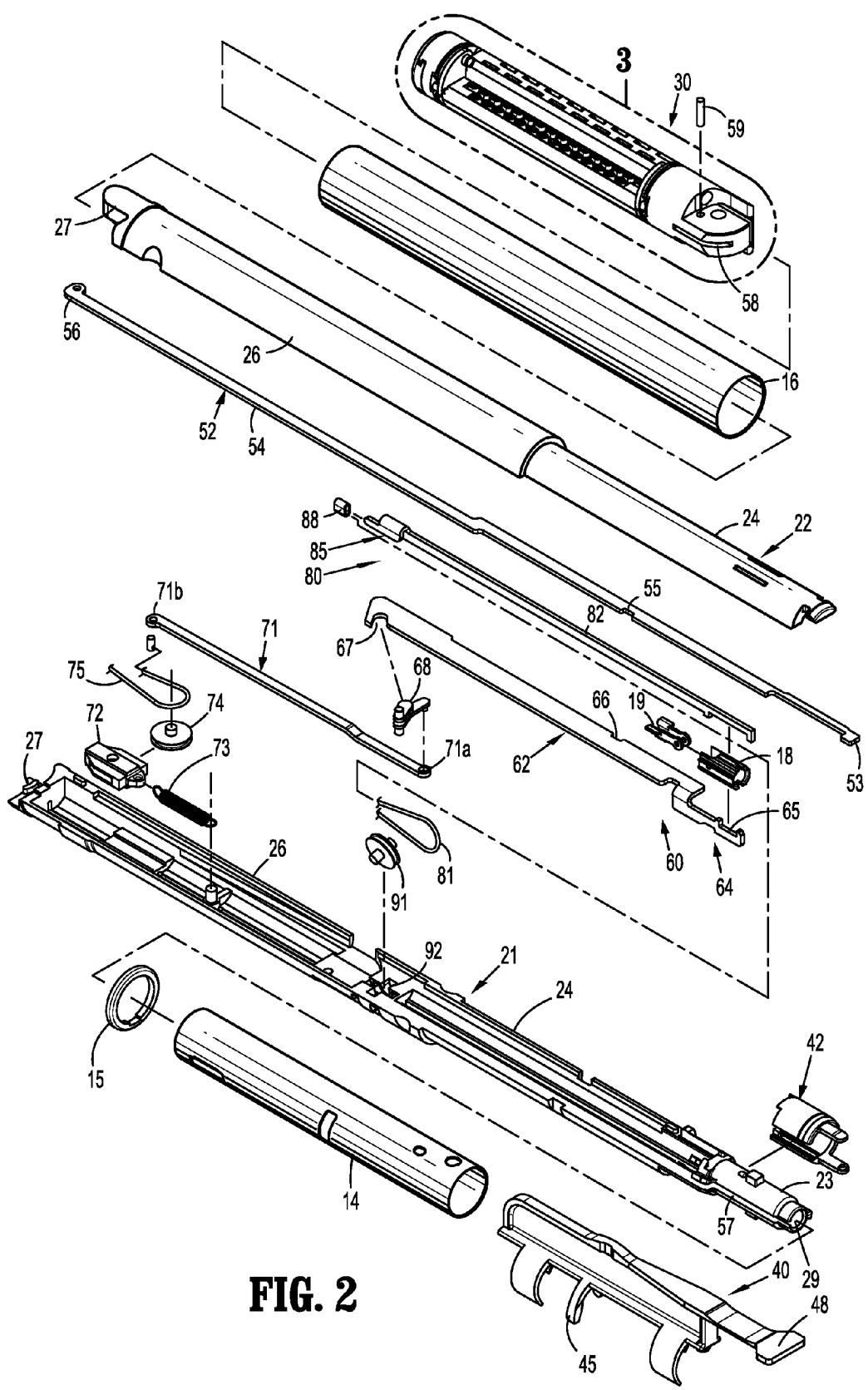
FIG. 2 is an exploded view with parts separated illustrating the internal components of the loading unit of FIG. 1.
Figure 3:
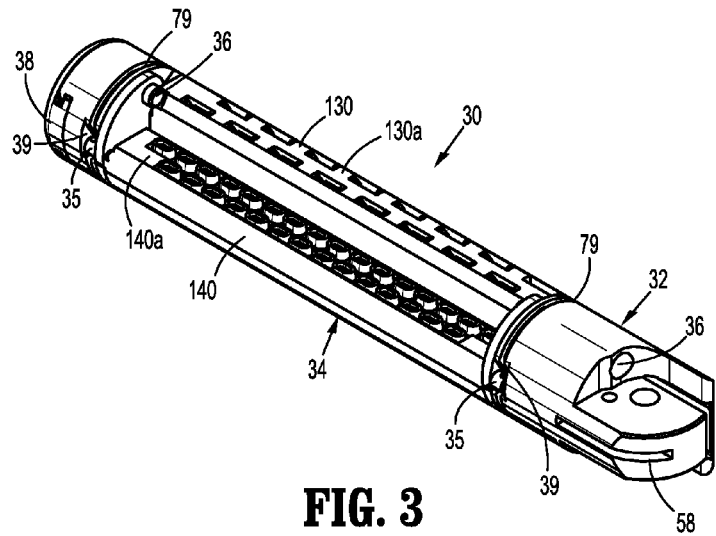
FIG. 3 is an enlarged view of the indicated area of detail of FIG. 2.
Figure 4:
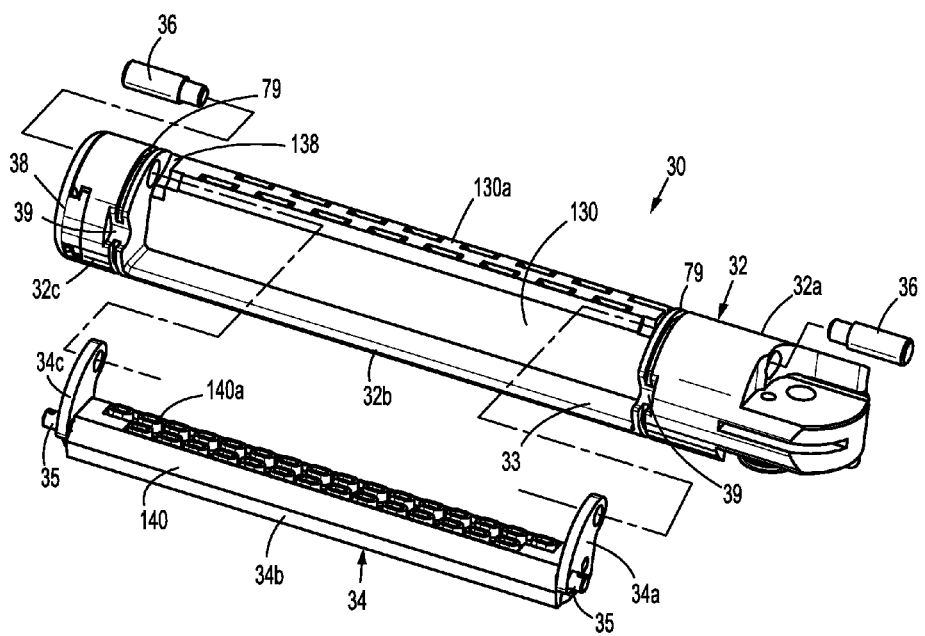
FIG. 4 is an exploded view with parts separated of the end effector of FIG. 3.

With additional reference to FIG. 2, the elongated body 12 includes an inner housing 20 formed from a lower housing portion 21 and an upper housing portion 22. The inner housing 20 includes the connector 23, a proximal cylinder 24, a distal cylinder 26, and a distal extension 27. The proximal cylinder 24 extends from the connector 23 and the distal cylinder 26 extends from the proximal cylinder 24. The distal cylinder 26 has a diameter that is larger than a diameter of the proximal cylinder 24. The distal extension 27 extends from the distal cylinder 26 and pivotally secures the end effector 30 to the inner housing 20. The lower housing portion 21 and the upper housing portion 22 are secured together by a proximal tube 14 disposed over the proximal cylinder 24 and a distal tube 16 disposed over the distal cylinder 26. The proximal tube 14 having a first diameter and the distal tube 16 having a second diameter greater than the first diameter. The first diameter may be in a range of about 5 mm to about 15 mm (e.g., 12 mm) and the second diameter may be in a range of about 12 mm to about 20 mm (e.g., 15 mm). The proximal tube 14 and the distal tube 16 may be joined by a housing ring 15 disposed over the proximal tube 14 and within the distal tube 16. The housing ring 15 may seal a gap defined between the proximal and distal tubes 14, 16. As shown in FIG. 1, the connector 23 extends proximally from proximal tube 14.

The housing 20 houses an articulation rod 52, a clamping mechanism 60, and a firing mechanism 80 that manipulate the end effector 30 as detailed below. The articulation rod 52 includes a proximal flag 53 and a body 54 extending from the proximal flag 52 to a distal end 56. The distal end 56 of the articulation rod 52 passes through an articulation slot 58 defined in the end effector 30 and is pivotally coupled to the end effector 30 by an articulation pin 59. The proximal flag 53 is longitudinally translatable in an articulation channel 57 defined in the connector 23 to articulate the end effector 30 relative to the elongated body 12 between a straight position (FIG. 38) and an articulated position (FIG. 39). In the straight position, the end effector 30 is substantially aligned with the elongated body 12 such that an angle defined between a longitudinal axis of the end effector 30 and a longitudinal axis of the elongated body 12 is in a range of about 175° to about 185° (e.g., 0° or 180°). In other words, the longitudinal axis of the end effector 30 may be articulated in a range of about 5° to about −5° (e.g., 0°) from the longitudinal axis of the elongated body 12 in the straight position. In a fully articulated position (not explicitly shown), the angle defined between the longitudinal axis of the end effector 30 and a longitudinal axis of the elongated body 12 is in a range of about 75° to about 105° (e.g., 90°). In other words, the longitudinal axis of the end effector 30 may be articulated in a range of about 75° to about 105° (e.g., 90°) from the longitudinal axis of the elongated body 12 in the fully articulated position. It will be appreciated that the end effector 30 may be articulated at any angle between the straight position and the fully articulated position. As detailed in greater detail below, the body 54 defines an articulation locking notch 55 that is engaged by the shipping wedge 40 to lock the end effector 30 in a shipping position (FIG. 1) between the straight position and the fully articulated position.

Figure 5:
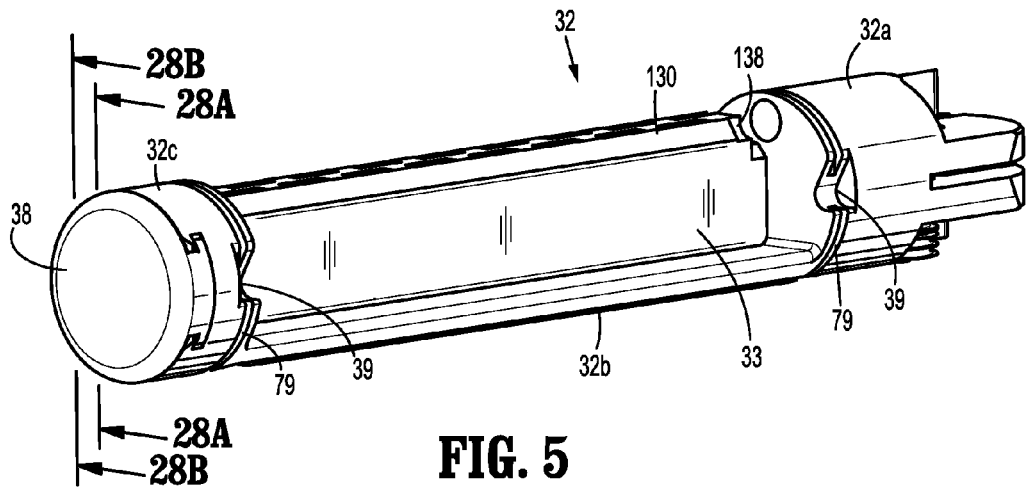
FIG. 5 is a perspective view of the fastener jaw of the end effector of FIG. 4.
Figure 6:
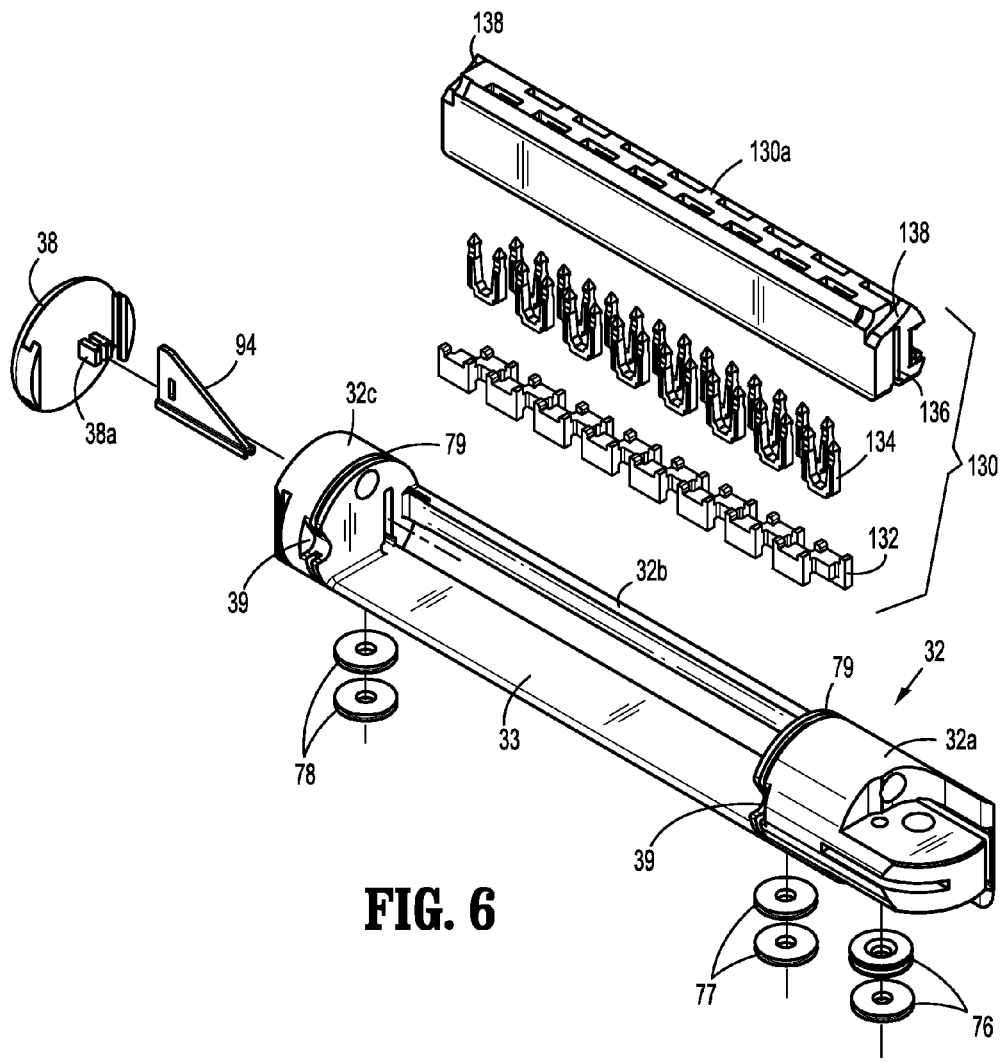
FIG. 6 is an exploded view with parts separated of the fastener jaw of FIG. 5.

Referring to FIGS. 3-7, the end effector 30 includes a fastener jaw 32 and a retainer jaw 34 that is rotatably coupled to the fastener jaw 32 by pins 36. With particular reference to FIGS. 5 and 6, the fastener jaw 32 includes a proximal portion 32a, a central portion 32b, and a distal portion 32c. The central portion 32b is disposed between the proximal and distal portions 32a, 32c and is configured to releasably couple a fastener cartridge 130 to the fastener jaw 32. The fastener cartridge 130 includes a plurality of pushers 132 and a plurality of fasteners 134. The central portion 32b defines a cavity 33 for rotatably receiving the retainer jaw 34. The retainer jaw has a distal end and a proximal end that are each pivotally connected to the fastener jaw so that the retainer jaw is pivotable about a longitudinal axis of the end effector. The walls of the proximal and distal portions 32a, 32c define annular grooves 79 adjacent the central portion 32b and define folded stop recesses 39 in the annular grooves 79 adjacent the cavity 33. In addition, the fastener cartridge 130 defines clamp stop recesses 138 (FIG. 6) adjacent the walls of the proximal and distal portions 32a, 32c. The fastener jaw 32 includes an end cap 38 having a sled retainer 38a that releasably retains a sled 94. The sled 94 is slidable through a sled channel 136 (FIG. 6) defined through the cartridge 130 to eject the plurality of fasteners 134 from the fastener cartridge 130 as detailed below. Further, as detailed below, idler pulleys 76, proximal pulleys 77, and distal pulleys 78 are rotatably coupled to a lower surface of the fastener jaw 32.

Figure 7:
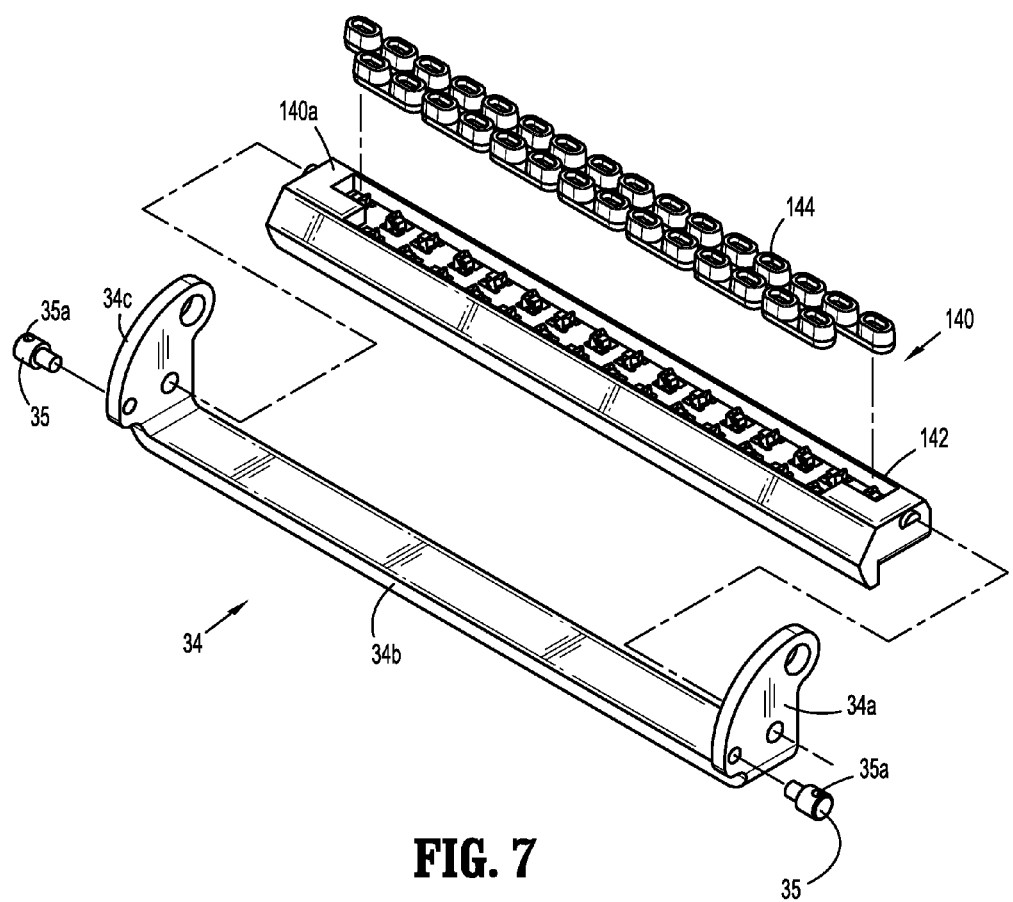
FIG. 7 is an exploded view with parts separated of the retainer jaw of FIG. 4.

With particular reference to FIG. 7, the retainer jaw 34 includes proximal and distal flanges 34a, 34c, at the proximal and distal ends, and a central portion 34b extending between the proximal and distal flanges 34a, 34c. Each of the proximal and distal flanges 34a, 34c includes a cable pin 35 extending away from the central portion 34b. Each cable pin 35 includes a cable passage 35a that couples to a clamping cable 75 (FIG. 20) as detailed below. The central portion 34b is configured to releasably couple a retainer cartridge 140 to the retainer jaw 34. The retainer cartridge 140 includes a body 142 that releasably retains a plurality of retainers 144. Referring back to FIG. 4, the proximal and distal flanges 34a, 34c are rotatably coupled to the fastener jaw 32 by pins 36.

Figure 8A:
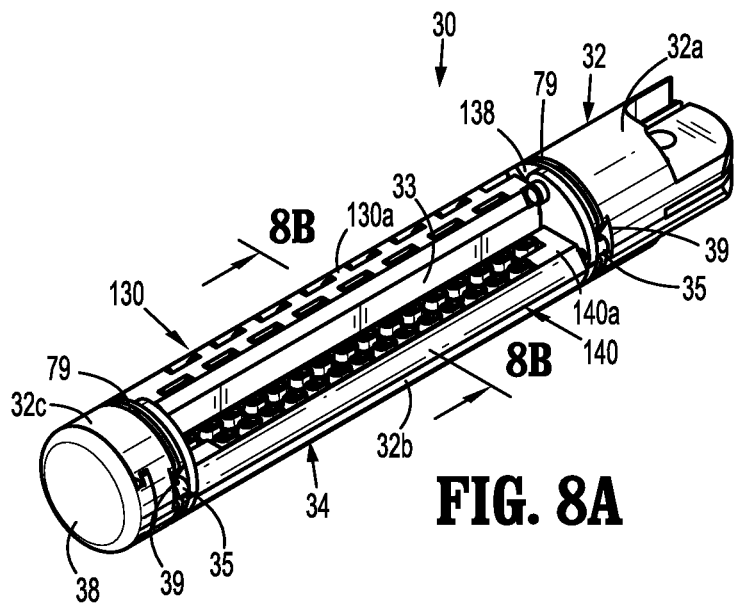
FIG. 8A is a perspective view of the end effector of FIG. 3 with the retainer jaw in a folded position.
Figure 9A:
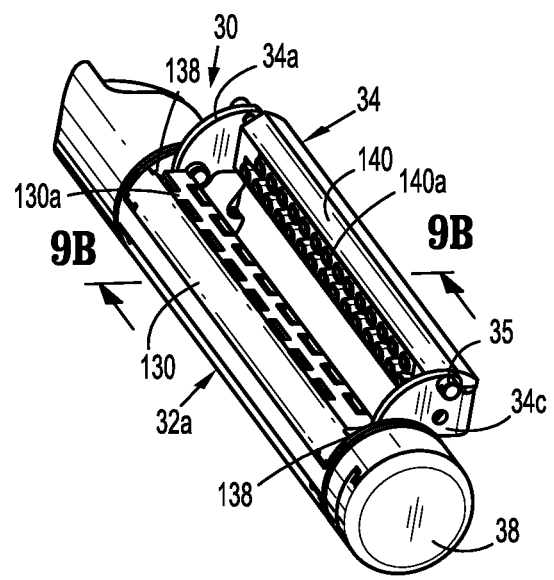
FIG. 9A is a perspective view of the end effector of FIG. 3 with the retainer jaw in an open position.
Figure 10A:
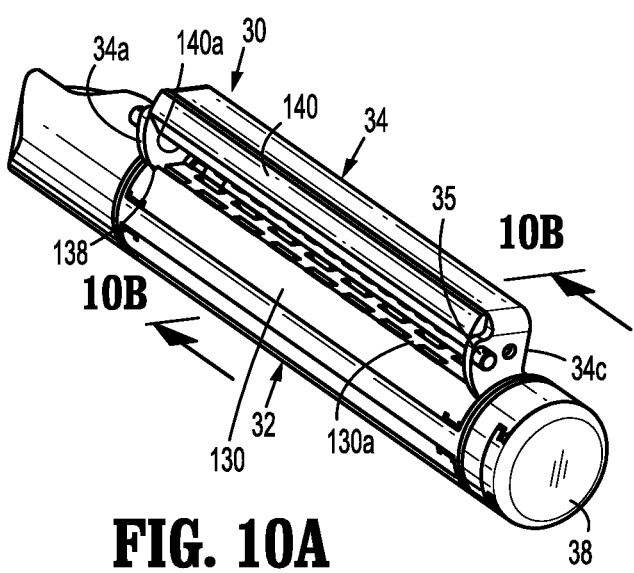
FIG. 10A is a perspective view of the end effector of FIG. 3 with the retainer jaw in a clamped position.
Figure 8B:
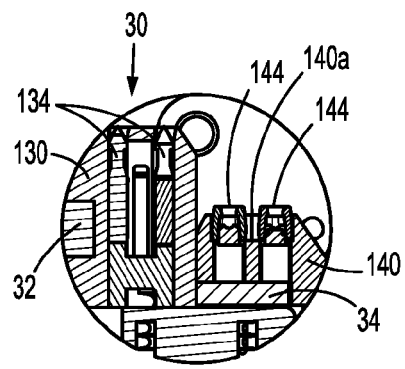
FIG. 8B is a cross-sectional view taken along the section line 8B-8B of FIG. 8A.
Figure 9B:
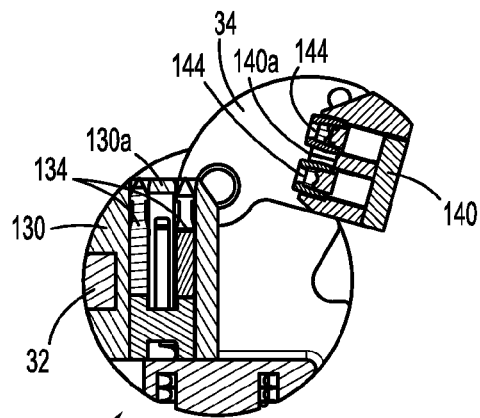
FIG. 9B is a cross-sectional view taken along the section line 9B-9B of FIG. 9A.
Figure 10B:
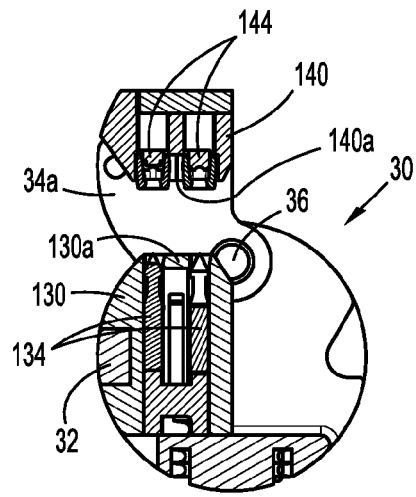
FIG. 10B is a cross-sectional view taken along the section line 10B-10B of FIG. 10A.

With reference to FIGS. 8A-10B, the end effector 30 has a folded position (FIGS. 8A and 8B), an open position (FIGS. 9A and 9B), and a clamped position (FIGS. 10A and 10B). In the folded position, the retainer jaw 34 is completely disposed within the cavity 33 defined in the central portion 32b of the fastener jaw 32 such that the end effector 30 is substantially cylindrical and has a substantially uniform outer diameter from the proximal portion 32a of the fastener jaw 32 to the distal portion 32c of the fastener jaw 32. When the end effector 30 is in the folded position, tissue contacting surfaces 130a, 140a of the fastener and retainer cartridges 130, 140, respectively, face in the same direction (e.g., up as shown in FIG. 8A). In the folded position, the cable pins 35 of the retainer jaw 32 are received within the folded stop recesses 39 defined in the annular grooves 79.

In the open position of the end effector 30, the fastener and retainer jaws 32, 34 are open relative to one another (i.e., between the folded and clamped positions). In a shipping configuration of the loading unit 10 (FIG. 1), the end effector 30 is in a particular open position, as shown in FIGS. 9A and 9B, with the tissue contacting surface 140a of the retainer cartridge 140 substantially perpendicular to the tissue contacting surface 130a of the fastener cartridge 130. As detailed below, the end effector 30 may be secured in the shipping configuration by the shipping wedge 40 (FIG. 1) such that the fastener cartridge 130 and the retainer cartridge 140 may be coupled to or decoupled from the fastener jaw 32 and the retainer jaw 34, respectively.

In the clamped position of the end effector 30, the tissue contacting surfaces 130a, 140a of the fastener and retainer cartridges 130, 140, respectively, oppose one another. In the clamped position, each fastener 134 of the fastener cartridge 130 is aligned with a respective retainer 144 of the retainer cartridge 140 such that when the fasteners 134 are ejected from the fastener cartridge 130, the fasteners 134 form two-part fasteners with the retainers 144 through tissue between the tissue contacting surfaces 130a, 140a of the fastener and retainer jaws 130, 140, respectively. In the clamped position, the proximal and distal flanges 34a, 34c of the retainer jaw 34 are received within the clamp stop recesses 138 (FIG. 10A) of the fastener cartridge 130 to prevent over rotation of the retainer jaw 34.

Figure 11:
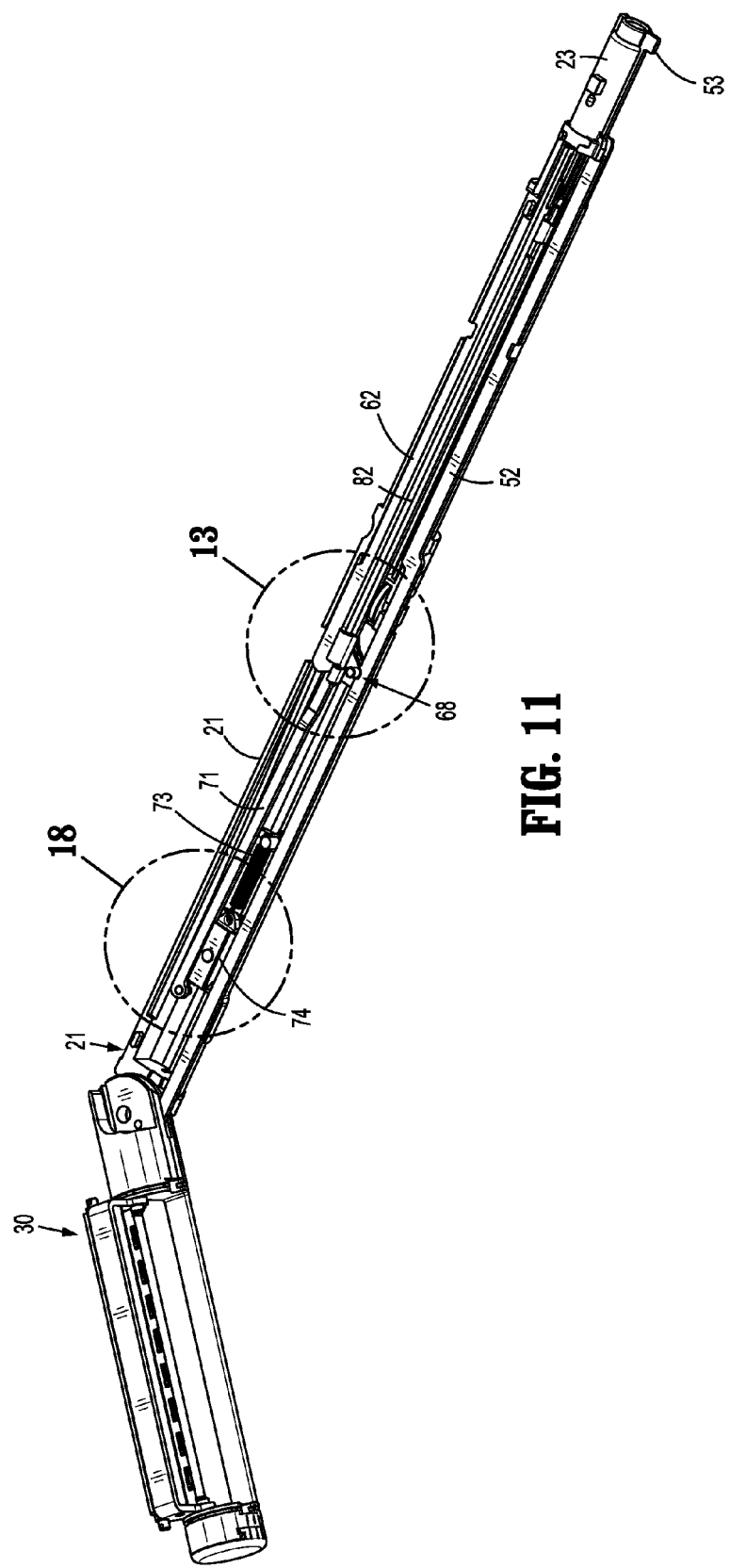
FIG. 11 is a perspective view of the loading unit of FIG. 1 with an upper housing portion removed.
Figure 12:
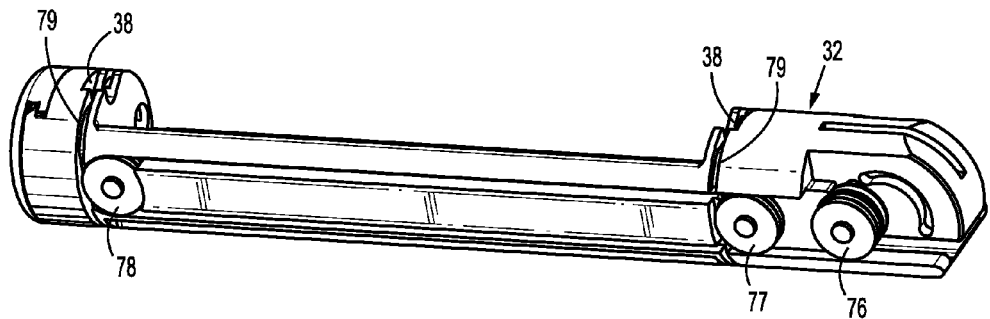
FIG. 12 is a bottom perspective view of the end effector of FIG. 3.
Figure 13:
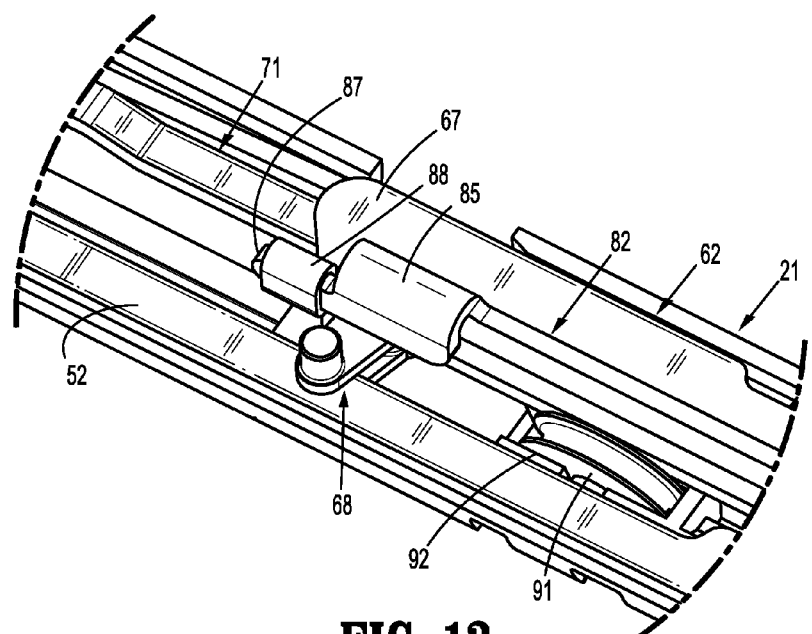
FIG. 13 is an enlarged view of the indicated area of detail of FIG. 11.

With reference to FIGS. 11-22, the clamping mechanism 60 converts translation of a clamping shaft 62 to rotation of the end effector 30 between the folded and clamped positions. With particular reference to FIG. 11, the clamping mechanism 60 includes a clamping shaft 62, a pivot arm 68, a clamping rod 71, and a clamping pulley 74 disposed within the housing 20 (FIG. 1) of the elongated body 12. The clamping mechanism 60 also includes idler pulleys 76, proximal pulleys 77, and distal pulleys 78 disposed on a lower surface of the fastener jaw 32 as shown in FIG. 12.

Referring briefly back to FIG. 2, the clamping shaft 62 includes a proximal portion 64 that defines a carriage notch 65 that receives a carriage 18 which is disposed within a carriage channel 29 defined in the connector 23. The carriage 18 is configured to translate in response to a drive rod (not shown) of a surgical instrument coupled to the connector 23.

Figure 14:
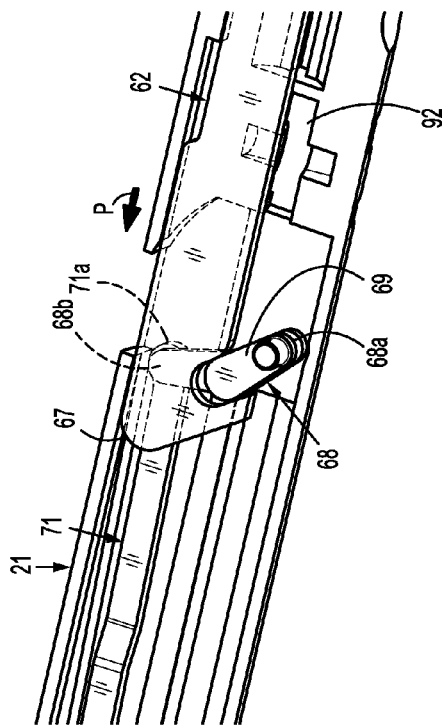
FIG. 14 is a perspective view of the clamping mechanism of FIG. 13 in a folded position.
Figure 17:
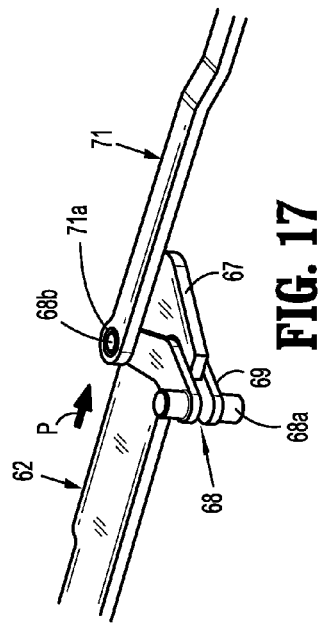
FIG. 17 is a bottom perspective view of the clamping mechanism of FIG. 13.
Figure 15:
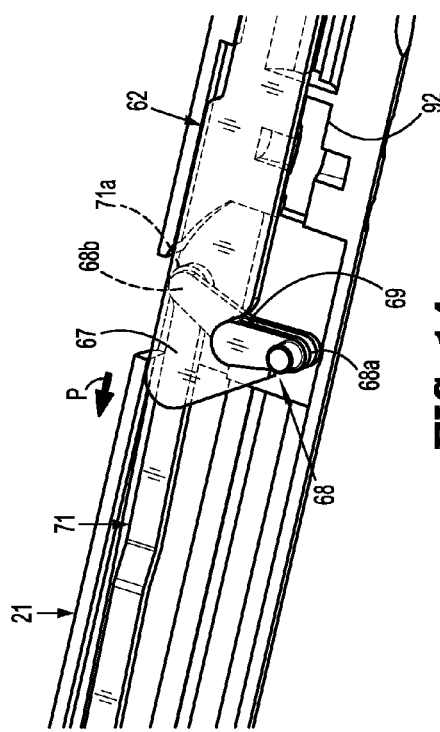
FIG. 15 is a perspective view of the clamping mechanism of FIG. 13 in an open position.
Figure 16:
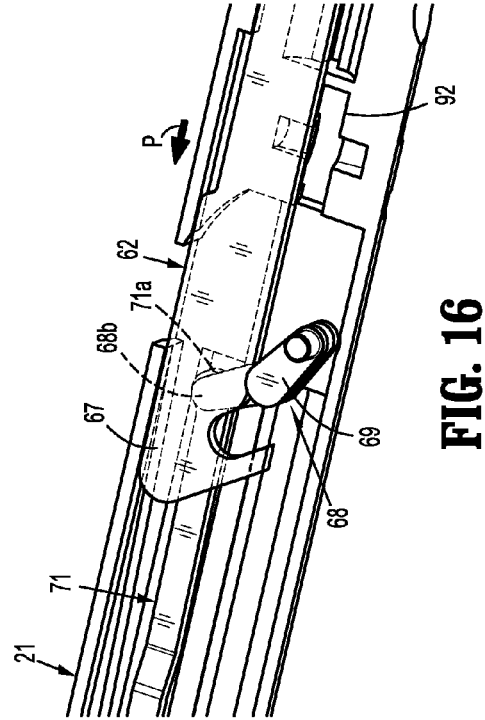
FIG. 16 is a perspective view of the clamping mechanism of FIG. 13 in a clamped position.

Now with reference to FIGS. 13-17, the clamping shaft 62 includes a distal portion which defines a cam or clamping hook 67. The clamping hook 67 slidingly engages the pivot arm 68 to pivot the pivot arm 68 between a folded position (FIG. 14) corresponding to the folded configuration of the end effector 30 (FIG. 8A), an open position (FIG. 15) corresponding to an open position of the end effector 30 (FIG. 9A), and a clamped position (FIG. 16) corresponding to the clamped position of the end effector 30 (FIG. 10A). The pivot arm 68 includes a first end 68a, a second end 68b, and a cam follower or engagement portion 69. The pivot arm 68 is rotatable about a first end 68a that is rotatably secured within the lower housing portion 21 of the inner housing 20 (FIG. 1). The first end 68a of the pivot arm 68 may also be rotatably secured by the upper housing portion 22 (FIG. 2) of the inner housing 20. The second end 68b is rotatably coupled to a proximal end 71a of the clamping rod 71. The engagement portion 69 is engaged by the clamping hook 67 of the clamping shaft 62 to rotate the pivot arm 68 about its first end 68a. As the pivot arm 68 pivots about its first end 68a, the pivot arm 68 translates the clamping rod 71. As the clamping shaft 62 is advanced as indicated by arrow "P", the clamping hook 67 cams the engagement portion 69 of the pivot arm 68 to rotate the pivot arm 68 towards the clamped position (FIG. 16). As the clamping shaft 62 is retracted opposite arrow P, the clamping hook 67 cams the engagement portion 69 of the pivot arm 68 to rotate the pivot arm 68 towards the folded position (FIG. 14). The clamping hook 67 of the clamping shaft 62 may be advanced past the pivot arm 68 such that the pivot arm 68 remains in the clamped position (FIG. 16) until the clamping shaft 62 is retracted to reengage the engagement portion 69 of the pivot arm 68 with the clamping hook 67. The clamping shaft 62 defines a clamping lock notch 66 (FIG. 2) that is engagable by the shipping wedge 40 (FIG. 1) to secure the clamping mechanism 60 in a shipping position, which is a particular open position corresponding to the shipping position of the end effector 30 and the shipping configuration of the loading unit 10.

Figure 18:
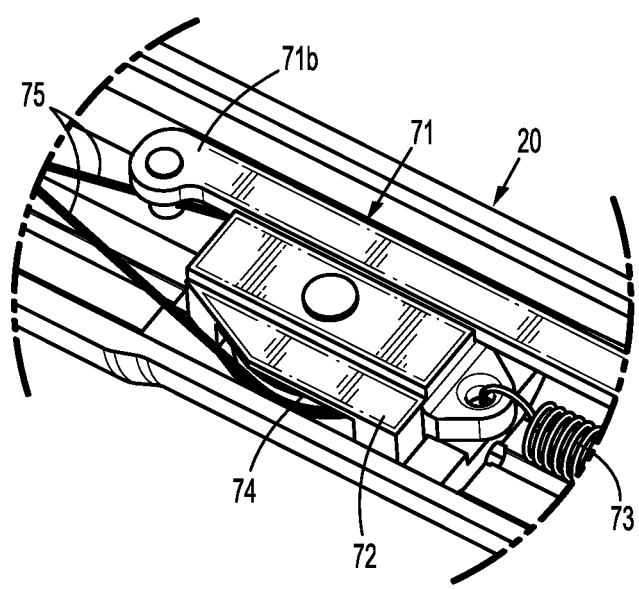
FIG. 18 is an enlarged view of the indicated area of detail of FIG. 11.
Figure 19:
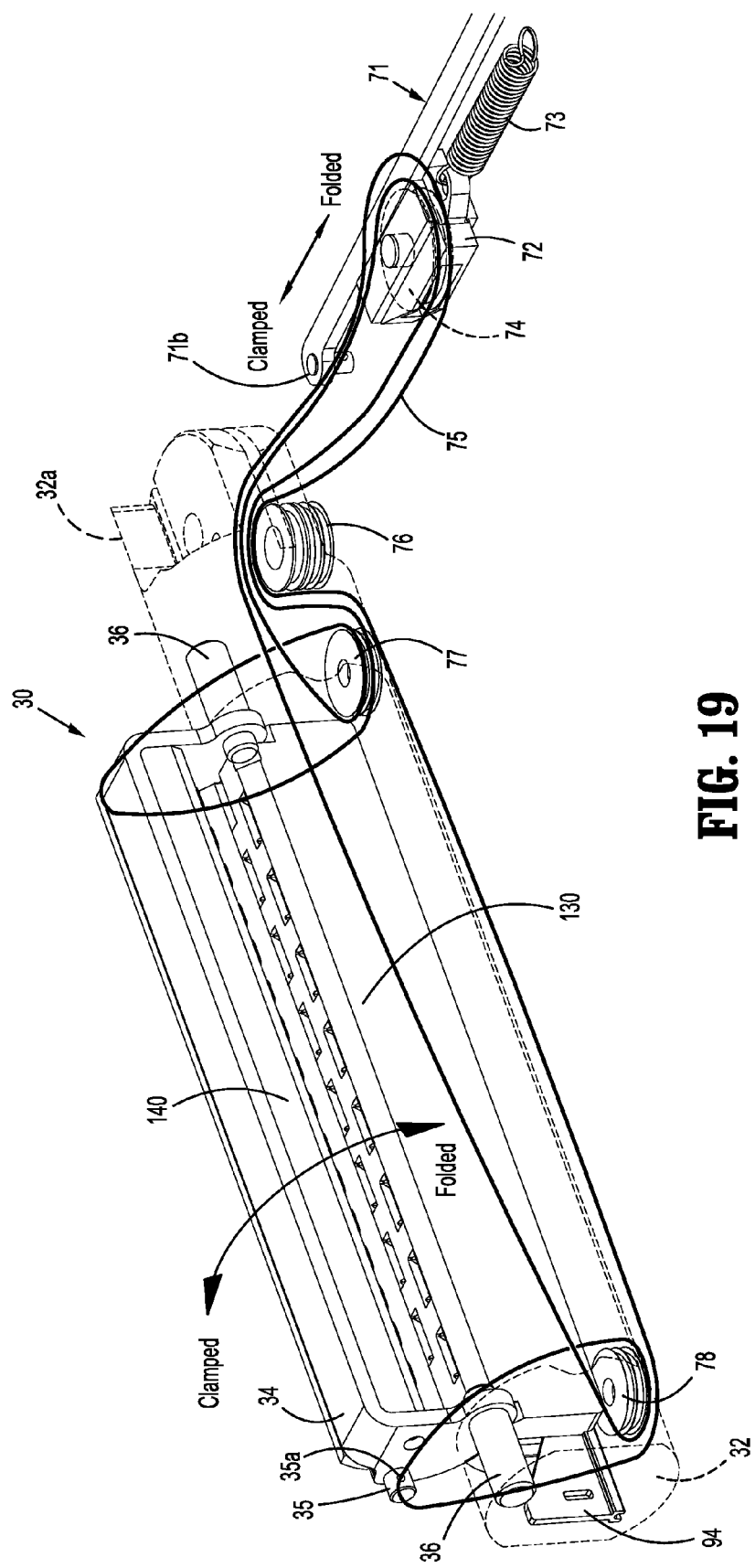
FIG. 19 is a perspective view illustrating the path of the clamping cable with portions of the elongated body removed and portions of the end effector shown in dashed lines.

Referring now to FIGS. 18 and 19, the distal end 71b of the clamping rod 71 is crimped or coupled to the clamping cable 75. The distal end 71b of the clamping rod 71 may include a pin that is crimped or coupled to the clamping cable 75. The clamping cable 75 is a continuous cable passing from the inner housing 20, through the end effector 30, and back into the inner housing 20. The clamping cable 75 extends proximally from the distal end 71b of the clamping rod 71 and around the clamping pulleys 74. The clamping pulleys 74 are mounted to a cable tensioner 72 that is attached to a biasing member 73. The biasing member 73 (FIG. 11) is secured to the lower housing portion 21 to pretension the clamping cable 75. From the cable pulleys 74, the clamping cable 75 exits through the proximal end of the inner housing 20 and into the end effector 30. The clamping cable 75 passes around the idler pulleys 76 and around the proximal pulleys 77 of the end effector 30. The pretension applied by the cable tensioner 72 prevents the retainer jaw 34 from rotating as the end effector 30 is articulated relative to the housing 20.

The clamping cable 75 extends from the proximal pulleys 77 and around the distal pulleys 78. From the distal pulleys 78, the clamping cable 75 passes through the fastener jaw 32 and into the annular groove 79. The clamping cable 75 extends from the annular groove 79 and through the cable pin 35 coupled to the distal flange 34c of the retainer jaw 34. The clamping cable 75 is coupled or crimped within the cable passage 35a of the cable pin 35 such that the clamping cable 75 is fixed relative to the cable pin 35. From the cable pin 35, the clamping cable 35 returns to the annular groove 79 and back around the distal pulleys 78. From the distal pulleys 78, the clamping cable 35 passes by the proximal pulleys 77 and around the idler pulleys 76. From the idler pulleys 76, the clamping cable 75 reenters the inner housing 20 and is coupled to the distal end 71b of the clamping rod 71.

Another portion of the clamping cable 75 extends proximally from the distal end 71b of the clamping rod 71 and around the clamping pulley 74. From the cable pulley 74, the clamping cable 75 exits through the proximal end of the inner housing 20 and into the end effector 30. The clamping cable 75 passes around the idler pulleys 76 and around the proximal pulleys 77 of the end effector 30. The clamping cable 75 extends from the proximal pulleys 77 into the annular groove 79 defined in the proximal portion 32a of the fastener jaw 32. The clamping cable 75 extends from the annular groove 79 and through the cable pin 35 coupled the proximal flange 34a of the retainer jaw 34. The cable pin 35 is coupled or crimped to the clamping cable 75 such that the clamping cable is fixed relative to the cable pin 35. From the cable pin 35, the clamping cable 35 returns to the annular groove 79 and back around the proximal pulleys 77. From the proximal pulleys 77, the clamping cable 35 passes around the idler pulleys 76 and reenters the inner housing 20 and is coupled to the distal end 71b of the clamping rod 71.

Referring back to FIGS. 14-16 and with reference to FIGS. 20-22, as pivot arm 68 is pivoted from the folded position towards the clamped position, the clamping cable 75 rotates the retainer jaw 34 from the folded position (FIG. 20), through an open position (FIG. 21), and to the clamped position (FIG. 22). Specifically, as the pivot arm 68 is pivoted to distally extend the clamping rod 71, the distal end 71b of the clamping rod 71 tensions the portion of the clamping cable 75 that passes around the cable tensioner 72 such that the clamping cable 75 pulls the cable pins 35 in a counter-clockwise direction when viewed from the distal end of the end effector 30 as indicated by the arrows A in FIGS. 20-22 to rotate the retainer jaw towards the clamped position (FIG. 22). When the pivot arm 68 is pivoted towards the folded position, the distal end 71b of the clamping rod 71 tensions the clamping cable 75 entering the inner housing portion 20 directly from the distal end 71b of the clamping rod 71 to pull the cable pins 35 in a clockwise direction (i.e., opposite the direction indicated by arrows A in FIGS. 20-22) to rotate the retainer jaw 34 towards the folded position (FIG. 20).

Referring now to FIGS. 23-27, the firing mechanism 80 includes a fire rod 82 and a fire pulley 91 rotatably supported in the lower housing portion 21 (FIG. 13), a sled 94 slidingly disposed within the end effector 30 (FIG. 1), and a fire cable 81 extending from the fire rod 82 to the sled 94. The fire rod 82 includes a proximal fire flag 83a and a distal fire flag 83b positioned in a proximal portion of the fire rod 82. The proximal and distal fire flags 83a, 83b define a fire gap 84 between the proximal and distal fire flags 83a, 83b. The carriage 18 is received within the fire gap 84 between the proximal and distal fire flags 83, 83b. The fire rod 82 includes a distal portion 85 having a cable retainer 86 and a distal finger 87. The fire cable 81 passes through the cable retainer 86, around the distal finger 87, and is secured to the distal finger 87 by a cable retainer clip 88 secured or crimped over the distal finger 87 and the fire cable 81.

The fire cable 81 extends proximally from the distal finger 87 of the fire rod 82 and over the fire pulley 91 that is rotatably supported within a fire pulley opening 92 (FIGS. 2 and 13) defined in the lower housing portion 21. The fire cable 81 extends distally from the fire pulley 91 and around the idler pulley 76 of the end effector 30. From the idler pulley 76, the fire cable 81 extends through the end effector 30 and is attached to the sled 94.

As the carriage 18 is advanced through the connector 23 (FIG. 2), the carriage 18 moves within the fire gap 84 of the fire rod 82 until a firing surface 18a (FIG. 27) of the carriage 18 engages the distal fire flag 83b of the fire rod 82. The distance between the firing surface 18a of the carriage 18 and the distal flag 83b, indicated by dimension D, defines a clamping dwell or delay for advancing the firing rod 82 in response to advancement of the carriage 18. The clamping dwell is at least equal to the distance required to advance the clamping shaft 62 to a position where the clamping hook 67 is past the pivot arm 68 as shown in FIG. 16, such that the pivot arm 68 is in the clamped position, as detailed above. In other words, the clamping dwell prevents the firing rod 82 from being advanced before the end effector 30 is in the clamped position. When the loading unit 10 is attached to a manually actuated handle, the clamping dwell is equal to a first pull of a trigger or moveable handle such that a subsequent pull of the trigger or moveable handle ejects fasteners 134 from the fastener cartridge 130.

With the end effector 30 in the clamped position (FIG. 10A), the carriage 18 is advanced such that the firing surface 18a engages the distal flag 83b of the firing rod 82 to advance the fire rod 82 as indicated by the arrow B (FIG. 26). As the fire rod 82 is advanced, the fire rod 82 tensions the fire cable 81, which is secured to the distal finger 87 of the fire rod 82, about the fire pulley 91 to pull the fire cable 81 in the direction indicated by arrow C. As the fire cable 81 is tensioned about the fire pulley 91, the fire cable 81 pulls the sled 94 proximally through the channel 136 of the fastener cartridge 130 to eject the fasteners 134 from the fastener cartridge 130 as detailed below.

Figure 30:
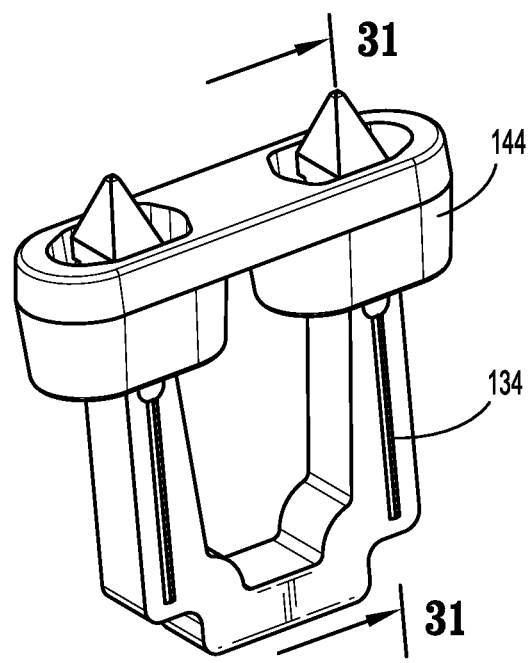
FIG. 30 is a perspective view of a completed two-part fastener of FIG. 29B.
Figure 31:
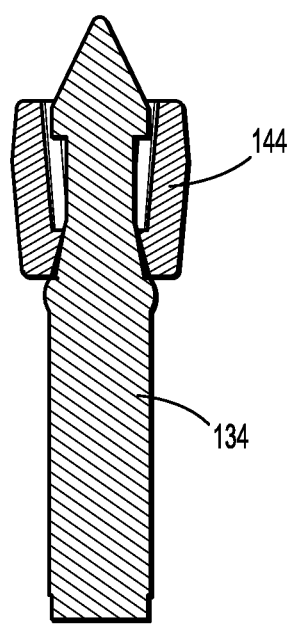
FIG. 31 is a cross-sectional view taken along the section line 31-31 of FIG. 30.

With reference to FIGS. 28A-29B, in an initial position (FIGS. 28A and 28B), the sled 94 is retained in the distal portion 32c of the fastener jaw 32 by a sled retainer 38a of the cap 38 and each of the fasteners 134 is positioned within the fastener cartridge 130. As the sled 94 is pulled proximally through the channel 136 as indicated by arrow F (FIG. 29A), an angled surface 95 of the sled 94 engages a camming surface 133 of the pushers 132 to move the pushers 132 towards the retainer jaw 34. Each pusher 132 is engaged with one or more fasteners 134 to eject the fastener 134 from the fastener cartridge 130 towards the retainer cartridge 140. As shown in FIGS. 30 and 31, each fastener 130 engages one or more of the retainers 140 to form a two-part fastener through tissue clamped between the fastener and retainer cartridges 130, 140.

In embodiments, the fasteners 134 may be unformed staples and the retainer jaw 32 may include an anvil (not shown). In such embodiments, the fasteners 134 are ejected from the fastener cartridge 130 such that the fasteners 134 interact with the anvil to form staples through tissue clamped between the fastener cartridge 130 and the anvil (i.e., deform legs of the unformed staples).

In some embodiments, the sled 94 is positioned in the proximal portion 32a of the fastener jaw 32 and is pulled distally by the fire cable 81 as the fire cable 81 is tensioned. In such embodiments, the fire cable 81 passes around the distal pulley 78 after passing around the idler pulley 76. It will be appreciated that in such embodiments the angled surface 95 of the sled 94 faces distally and the camming surface 133 of the pushers 132 face proximally.

In certain embodiments, the sled 94 includes a knife (not shown), that extends through a knife slot (not shown) to sever tissue between the fastener and retainer jaws 32, 34 as the sled 94 is pulled through the end effector 30. In particular embodiments, the knife (not shown) is separate from the sled 94 and is attached to the fire cable 81 independent of the sled 94.

Referring back to FIG. 27, when a desired number of fasteners 134 are ejected from the fastener cartridge 130, the carriage 18 is retracted such that the carriage 18 engages the proximal flag 83a of the fire rod 82 to retract the fire rod 82. As the fire rod 82 is retracted, the tension in the fire cable 81 is released such that the fire cable 81 is slack within the inner housing 20. As the tension is released from the fire cable 81, the sled 94 remains in position within the fastener cartridge 130.

Referring now to FIGS. 32-35, the loading unit 10 is provided with a shipping wedge 40 to secure the end effector 30 in a shipping configuration. In the shipping configuration, the end effector 30 is articulated relative to the elongated body 12 and the retainer jaw 34 is in an open position with respect to the fastener jaw 32. As shown in FIG. 1, in the shipping configuration, the end effector 30 is articulated about 45° with respect to the elongated body 12; however, it is contemplated that in the shipping configuration the end effector 30 may be articulated in a range of about 15° to about 60° with respect to the elongated body 12. Further, as shown FIGS. 9A and 9B, in the shipping configuration, the retainer jaw 34 is positioned such that when a retainer cartridge 140 is attached to the retainer jaw 34, the tissue contacting surface 140a of the retainer cartridge 140 is substantially perpendicular to the tissue contacting surface 130a of the fastener cartridge 130 attached to the fastener jaw 32. It is contemplated that in the shipping configuration, the retainer jaw 34 may be in any open position (i.e., between the folded position and the clamped position) that allows for the retainer cartridge 140 and the fastener cartridge 130 to be coupled and decoupled from the retainer jaw 34 and the fastener jaw 32, respectively.

With particular reference to FIGS. 33-35, the articulation rod 52 defines the articulation locking notch 55 and the clamping shaft 62 defines the clamping locking notch 66. In the shipping configuration, each of the locking notches 55, 66 is engaged by a respective locking finger 45, 46 of the shipping wedge 40. Specifically, an articulation locking finger 45 of the shipping wedge engages the articulation locking notch 55 of the articulation rod 52 and a clamping locking finger 46 of the shipping wedge 40 engages the clamping locking notch 46 of the clamping shaft 62. The engagement of the locking fingers 45, 46 with the locking notches 45, 46 fixes the articulation of the end effector 30 with respect to the elongated body 12 and the position of the retainer jaw 34 with respect to the fastener jaw 32. By fixing the articulation of the end effector 30 and the position of the retainer jaw 34, the fastener cartridge 130 and the retainer cartridge 140 can be coupled and decoupled from the fastener jaw 32 and the retainer jaw 34, respectively, without moving the articulation assembly 50, the clamping mechanism 60, and the firing mechanism 80. Further, fixing the articulation of the end effector 30 and the position of the retainer jaw 34, the loading unit 10 may be attached and detached from a surgical instrument without unintentional movement of the end effector 30 or retainer jaw 34. It is contemplated that the shipping wedge 40 may also include support fingers 47 to support the shipping wedge 40 on the proximal tube 14 of the elongated body 12.

With reference to FIGS. 1, 36, and 37, the shipping wedge 40 is secured to the loading unit 10 by a locking ring 42 engaged with a hook 41 of the shipping wedge 40. The locking ring 42 includes a locking shelf 43 and proximal fingers 44. The locking ring 42 is rotatably positioned over the connector 23 of the inner housing 20. In a locked position of the locking ring 42 (FIGS. 1 and 36), the locking shelf 43 of the locking ring 42 engages the hook 41 of the shipping wedge 40 to secure the shipping wedge 40 to the loading unit 10. When the loading unit 10 is coupled to an adapter (not shown) or a surgical instrument (not shown), the connector 23 is secured to the adapter or surgical instrument by a bayonet type connection such that the adapter or surgical instrument engages the proximal fingers 44 of the locking ring 42 to rotate the locking ring 42 to an unlocked position (FIG. 37) such that the locking shelf 43 is rotated out of engagement with the hook 41. With the locking ring 42 in the unlocked position, a release tab 48 of the shipping wedge 40 is engaged to remove the shipping wedge 40 from the loading unit 10.

Referring now to FIGS. 38-41, the loading unit 10 is used during a Total Laparoscopic Hysterectomy (TLH) procedure to close the vaginal cuff VC. To begin the loading unit 10 is loaded by coupling a fastener cartridge 130 and a retainer cartridge 140 to the fastener jaw 32 and the retainer jaw 34, respectively. The loading unit 10 may be supplied in a preloaded condition or may be supplied in a kit with one or more pairs of fastener and retainer cartridges with varying lengths and types of fasteners (e.g., 2 mm, 3 or 3.5 mm, 4 or 4.8 mm, or 5 mm two-part fasteners or deformable staples). With the fastener cartridge 130 and the retainer cartridge 140 coupled to the end effector 30, the loading unit 10 is attached to a surgical instrument (not explicitly shown). When the loading unit 10 is attached to the surgical instrument, the locking ring 42 is rotated from a locked position to an unlocked position. With the locking ring 42 is in the unlocked position, the release tab 48 is engaged to remove the shipping wedge 40 from the loading unit 10. It is contemplated that the loading unit 10 may be attached to the surgical instrument before the fastener and retainer cartridges 130, 140 are coupled to the end effector 30.

With the shipping wedge 40 removed from the loading unit 10, the end effector 30 is articulated to a straight position relative to the elongated body 12 such that the end effector 30 is substantially aligned with the elongated body 12. In addition, the retainer jaw 32 is rotated into the folded position such that the end effector 30 is substantially cylindrical along its length and has a substantially uniform outer diameter.

Figure 38:
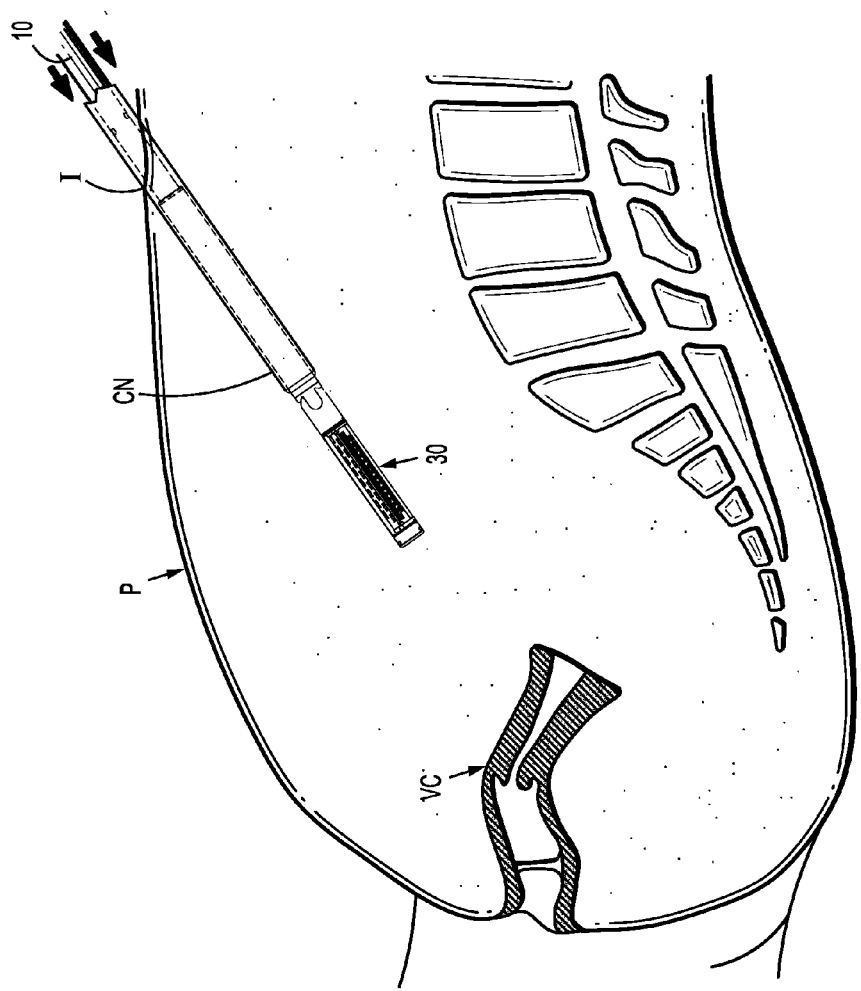
FIG. 38 is a cut-away view of the loading unit of FIG. 1 in use during a surgical procedure in accordance with the present disclosure with the loading unit in a straight configuration.
Figure 39:
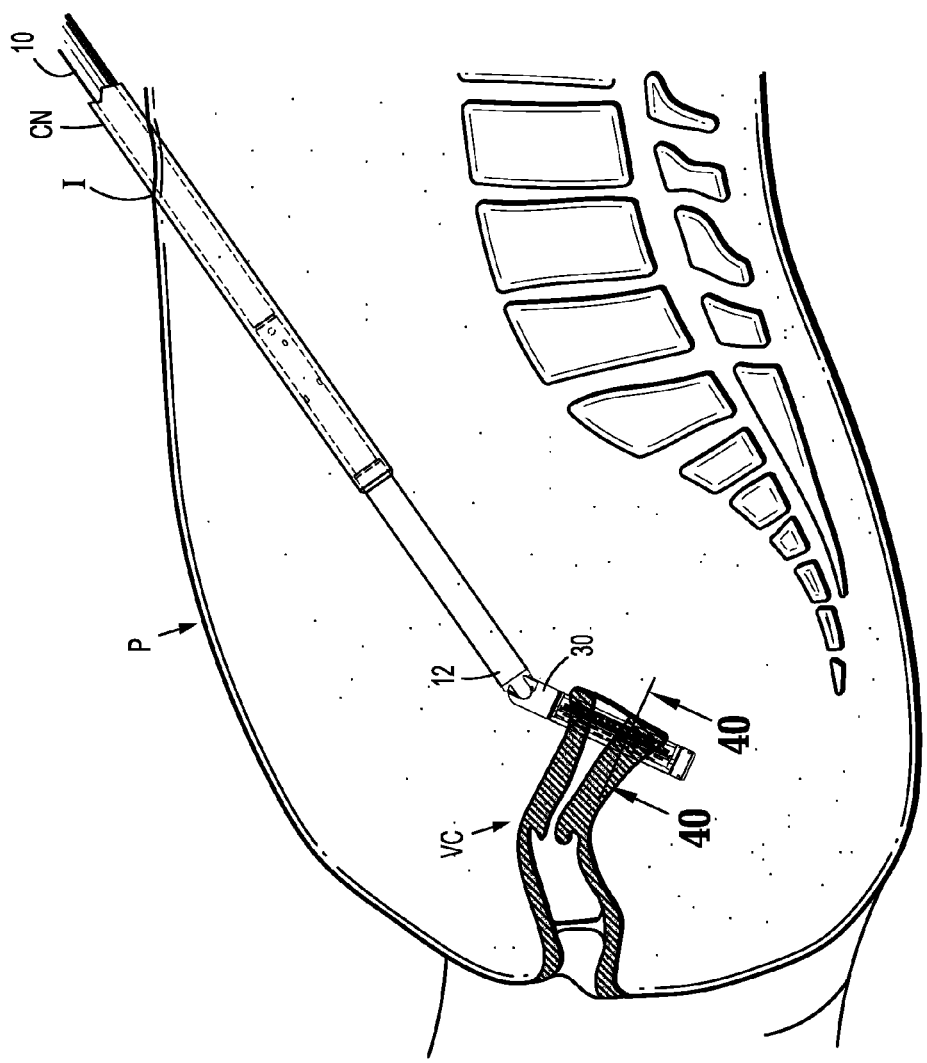
FIG. 39 is a cut-away view of the loading unit of FIG. 38 with the end effector positioned adjacent an end of a vaginal cuff in a folded position.

With particular reference to FIG. 38, with the end effector 30 in the straight position and the retainer jaw 32 in the folded position, the loading unit 10 is inserted through a surgical site S of a patient P to access a vaginal cuff VC. As shown, the loading unit 10 is inserted through a cannula CN positioned through an opening (e.g., a naturally occurring opening or an incision I) to access a surgical site within the body cavity of the patient P.

Figure 40:
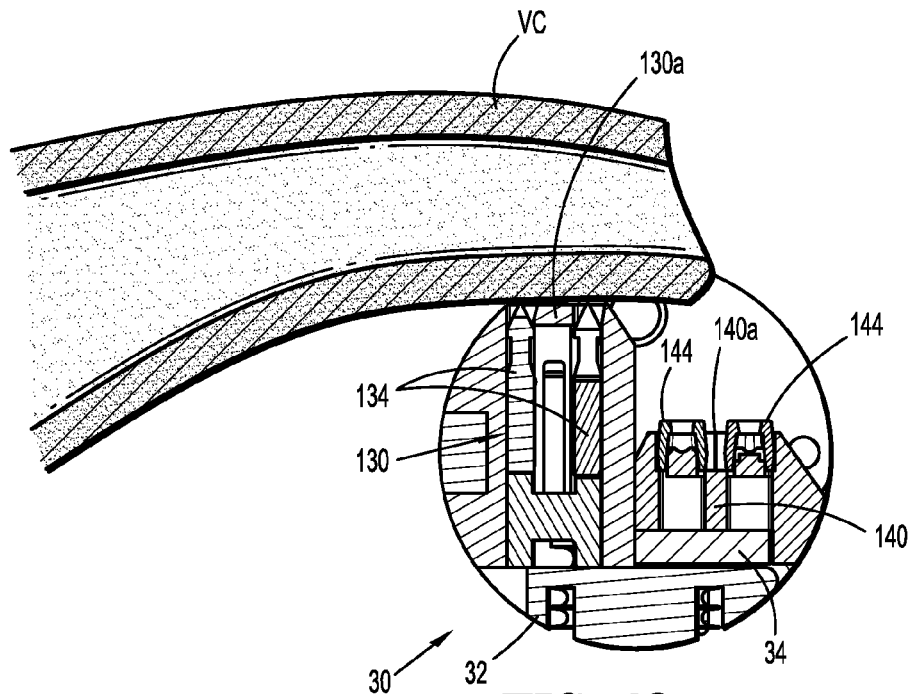
FIG. 40 is a cross-sectional view taken along the section line 40-40 of FIG. 39.
Figure 41:
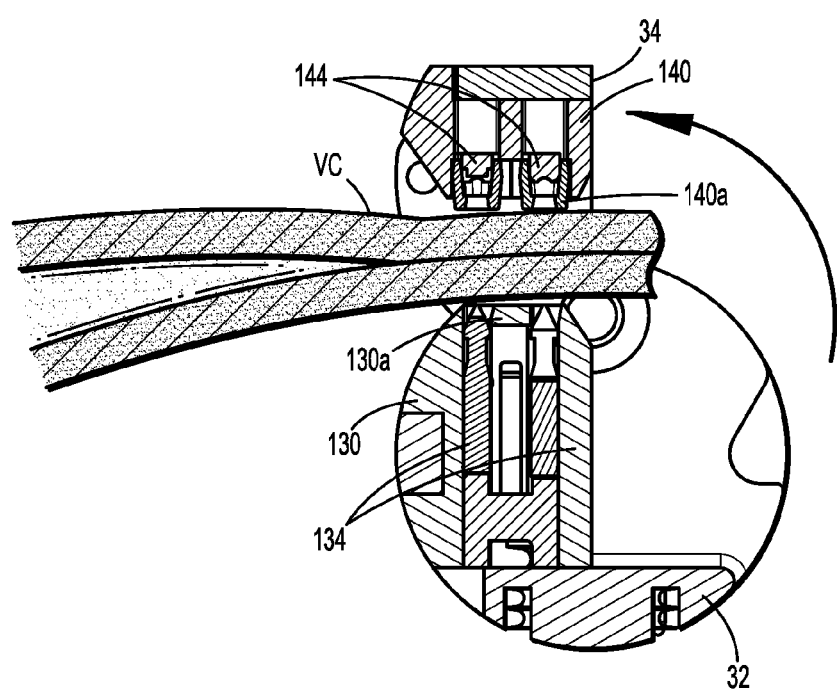
FIG. 41 is a cross-sectional view of the end effector of FIG. 40 in a clamped position.

Referring now to FIGS. 39 and 40, the end effector 30 is positioned adjacent an open end of the vaginal cuff VC and is articulated such that the end effector 30 is substantially perpendicular to the vaginal cuff VC. The retainer jaw 34 is positioned closer to the open end of the vaginal cuff VC with respect to the fastener cartridge 130 with the vaginal cuff VC positioned between the proximal and distal flanges 34a, 34c of the retainer jaw 34. The loading unit 10 is then manipulated to advance the carriage 18 to engage the clamping mechanism 60 to rotate the retainer jaw 34 from the folded position to the clamped position as shown in FIG. 41. As the retainer jaw 34 is rotated, the vaginal cuff VC is positioned between the fastener jaw 32 and the retainer jaw 34. As the vaginal cuff VC is positioned between the jaws 32, 34, the vaginal cuff VC may be flattened between the tissue contacting surfaces 130a, 140a of the fastener and retainer cartridges 130, 140.

With the vaginal cuff VC positioned between the jaws 32, 34, a clinician verifies that the open end of the vaginal cuff VC is beyond the fastener jaw 32. The loading unit 10 is then manipulated to further advance the carriage 18 to engage the firing mechanism 80 to pull the sled 94 through the fastener cartridge 130 to drive the fasteners 134 towards the retainers 144 to form two-part fasteners to close the vaginal cuff VC as detailed above. As detailed above, the fasteners 134 may also be deformable staples that are deformed to form staples to close the vaginal cuff VC. The fasteners 134 and the retainers 144 may be bioabsorbable such that the fasteners 134 and retainers 144 are absorbed as the anastomosis of the vaginal cuff VC is completed. It is contemplated that the fasteners 134 or the retainers 144 may be coated with a substance that aids in the anastomosis of the vaginal cuff VC.

Figure 42:
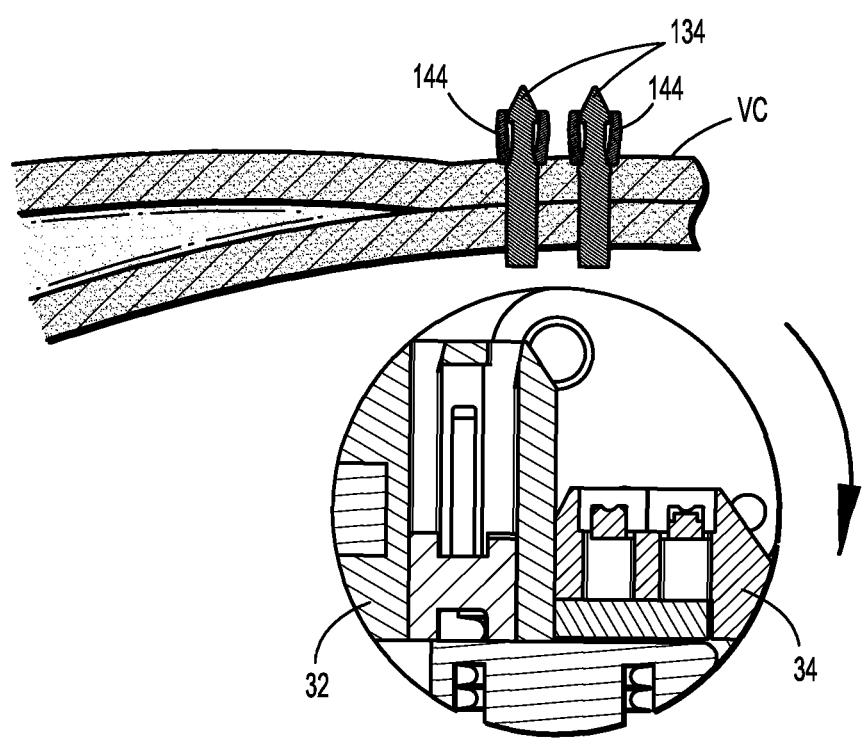
FIG. 42 is a cross-sectional view of the end effector of FIG. 41 returned to a folded position with fasteners ejected from the fastener cartridge, through the vaginal cuff, and into retainers of the retainer cartridge.

Referring to FIG. 42, after the fasteners 134 are ejected through the vaginal cuff VC, the retainer jaw 34 is rotated back to the folded position. As the retainer jaw 34 is returns to the folded position, the vaginal cuff VC is released from between the fastener jaw 32 and the retainer jaw 34. The end effector 30 is then articulated to the straight position such that the end effector 30 is aligned with the elongated body 12. With the end effector 30 in the straight position and the retainer jaw 34 in the folded position, the loading unit 10 is withdrawn from the surgical site S.

After the loading unit 10 is withdrawn from the surgical site S, the loading unit 10 may be detached from the surgical instrument. With the loading unit 10 separated from surgical instrument, the loading unit 10 may be sterilized for reuse in another surgical procedure.

Alternatively, the loading unit 10 may be reloaded by positioning loading unit 10 in the shipping configuration (i.e., articulating the end effector 30 to the shipping position and rotating the retainer jaw 34 to the shipping position). With the loading unit 10 in the shipping configuration the shipping wedge 40 may be coupled about the proximal tube 14 to fix the loading unit 10 in the shipping configuration. With the loading unit 10 in the shipping configuration, the fastener cartridge 130 and the retainer cartridge 140 may be decoupled from the fastener jaw 32 and the retainer jaw 34, respectively. Then, a new fastener cartridge and retainer cartridge may be coupled to the fastener jaw 32 and retainer jaw 34, respectively, such that the loading unit 10 may be reused during the same surgical procedure.

While the loading unit 10 is detailed above for performing a TLH, it is contemplated that the loading unit 10 may be used for closing a variety of tubular structures including, but not limited to, veins, arteries, and bowels.

In any of the embodiments disclosed herein an end effector can have a first jaw and a second jaw having a distal end and a proximal end, the distal end and the proximal end each being pivotally connected to the first jaw, the second jaw being pivotable about a longitudinal axis of the end effector. The first jaw can hold a plurality of fasteners, and the second jaw can have a plurality of retainers. In other embodiments, the end effector has a staple cartridge jaw and an anvil with staple forming recesses on the other jaw.

The end effector has a folded position, an open position, and a clamped position. In the folded position, the tissue contacting surfaces face in the same direction and the end effector has a circular envelope/profile. The end effector jaw can rotate or slide between its various positions.

The end effector can have a tetainer jaw with a cable pin with a hole for allowing the passage of a clamping cable. The end effector can have a cable for moving the position of the jaws, for firing, and/or for articulation. In certain embodiments, other means of actuating functions are used, such as threaded rotatable members, pushing rods, electronics, etc.

A method of clamping the jaws of a surgical fastening instrument, can include retracting a clamping shaft, a clamping hook of the clamping shaft camming an engagement portion of a pivot arm to rotate the pivot arm toward a folded position, the folded position of the pivot arm corresponding to a folded position of an end effector of the instrument. In certain embodiments, advancing the clamping hook past the pivot arm so that the claming hook disengages the pivot arm and keeps the end effector in the clamped position.

In certain embodiments, a combination of cables and push rods are used. A clamping cable can be connected to the clamping rod, for moving the jaws of the instrument. The clamping cable extends around pulleys and the pulleys have a tensioning device to pre-tension the clamping cable. The clamping cable has an end that extends through one jaw of the instrument, and an end that extends through the other jaw. A cam mechanism may be used to disconnect the clamping cable and push rod.

One end of the cable extends around one or more pulleys and is fixed to a cable pin of the second jaw or retainer jaw. The other end of the cable extends through fastener jaw and is fixed to the other cable pin of the second jaw or retainer jaw.

An end effector can have a firing rod defining a clamping delay. The clamping hook is disengaged from the clamping rod, maintaining the jaws in the clamped position, before the firing begins. In certain embodiments, a firing cable extends from a firing rod to a sled. A carriage moves within a fire gap in the fire rod to define a clamping delay before firing. After the clamping delay, the carriage engages the firing rod, which tensions the cable and pulls a sled proximally. A clamping mechanism with a delay may be used in any of the embodiments disclosed herein. The delay may be effected by a clamping shaft that engages and disengages a camming member (such as the pivot arm) so that further movement of the clamping shaft does not move the clamping rod and clamping cable while the end effector remains in the clamped position The device has two or three rows of fasteners and may have no knife. The device can deploy absorbable fasteners having one or two parts, surgical staples, clips or other fasteners. The sled can be parked in a distal portion of the end effector and moved proximally, or the sled can move distally starting from the proximal end. The pushers are desirably double or triple pushers; that is, the pushers desirably support two or three fasteners that are driven at the same time.

A shipping wedge can be included in any of the embodiments disclosed herein. The shipping wedge can prevent the movement of the articulation rod, and/or protect the sled from moving or may have other functions.

In certain embodiments, the end effector is part of a loading unit that is attachable to an adapter or handle, whether manual or powered. The articulation rod has flag or other engagement feature at a proximal end thereof. In certain embodiments, the flag must be in an intermediate position in order to attach the loading unit to the adapter, handle, or other actuator. A shipping wedge or shipping appliance is attached to the loading unit and has a member that engages the articulation rod, to maintain the intermediate position of the articulation rod. The shipping appliance may also maintain the position of the clamping shaft and/or firing rod.

Any of the embodiments disclosed herein can be used to close the vaginal cuff after a hysterectomy, or used to close some other hollow organ.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An end effector comprising:
   a first jaw having a proximal portion, a central portion, and a distal portion, the central portion having a first tissue contacting surface and defining a cavity, the first jaw defining an end effector axis; and
   a second jaw having a second tissue contacting surface and rotatably secured to the first jaw about a rotation axis, the rotation axis being parallel to the end effector axis, the second jaw having a folded position such that the second jaw is positioned within the cavity of the first jaw with the second tissue contacting surface of the second jaw facing the same direction as the first tissue contacting surface of the first jaw such that the end effector is cylindrical, the second jaw rotatable to a clamped position such that the second jaw is rotated about the rotation axis with the second tissue contacting surface of the second jaw in opposition to the first tissue contacting surface of the first jaw.

2. The end effector according to claim 1, wherein the first jaw includes a fastener cartridge having a plurality of fasteners.

3. The end effector according to claim 2, wherein the first jaw includes a sled translatable through the fastener cartridge to eject the plurality of fasteners from the first jaw towards the second jaw when the second jaw is in the clamped position.

4. The end effector according to claim 1, wherein the second jaw includes a proximal flange, a distal flange, and a central portion connecting the proximal and distal flanges.

5. The end effector according to claim 4, wherein proximal and distal portions of the first jaw each define a folded stop recess adjacent the cavity, wherein each of the proximal and distal flanges of the second jaw includes a stop pin extending away from the central portion of the second jaw, the stop pins received within the folded stop recesses when the second jaw is in the folded position.

6. The end effector according to claim 4, wherein the central portion of the first jaw defines clamp stop recesses adjacent the proximal and distal portions of the first jaw, the clamp stop recess configured to receive the proximal and distal flanges of the second jaw when the second jaw is in the clamped position.

7. A loading unit comprising:
   a housing including a connector positioned at a proximal end of the housing, the connector configured to couple the loading unit to a surgical instrument, the housing defining a longitudinal axis;
   an end effector supported at a distal end of the housing, the end effector including:
   a first jaw having a proximal portion, a central portion, and a distal portion, the central portion having a first tissue contacting surface and defining a cavity, the central portion including a plurality of fasteners, the first jaw defining an end effector axis; and
   a second jaw having a second tissue contacting surface and rotatably secured to the first jaw about a rotation axis, the rotation axis being parallel to the end effector axis, the second jaw having a folded position such that the second jaw is positioned within the cavity of the first jaw with the second tissue contacting surface of the second jaw facing the same direction as the first tissue contacting surface of the first jaw such that the end effector is cylindrical, the second jaw rotatable to a clamped position such that the second jaw is rotated about the rotation axis with the second tissue contacting surface of the second jaw in opposition to the first tissue contacting surface of the first jaw;

a clamping mechanism disposed within the housing and operatively associated with the second jaw to rotate the second jaw between the folded and clamped positions, the clamping mechanism including a clamping rod, a clamping shaft, and a pivot arm positioned between the clamping rod and the clamping shaft to longitudinally translate the clamping rod in response to longitudinal translation of the clamping shaft; and a firing mechanism disposed within the housing and operatively associated with the first jaw to eject the plurality of fasteners from the first jaw towards the second jaw when the second jaw is in the clamped position, the firing mechanism including a fire rod that is longitudinally translatable within the housing.

8. The loading unit according to claim 7, wherein a distal end of the clamping shaft includes a clamping hook, the pivot arm including a first end rotatably coupled to the housing, a second end coupled to a proximal end of the clamping rod, and a cam follower positioned between the first and second ends of the pivot arm, wherein the clamping hook engages the cam follower of the pivot arm to rotate the pivot arm between a folded position and a clamped position of the pivot arm, wherein rotation of the pivot arm effects translation of the clamping rod.

9. The loading unit according to claim 7, wherein the clamping rod is coupled to a clamping cable which is coupled to the second jaw, the clamping cable rotating the second jaw between the folded and clamped positions.

10. The loading unit according to claim 9, wherein distal translation of the clamping rod tensions the clamping cable to rotate the second jaw towards the clamped position and proximal translation of the clamping rod tensions the clamping cable to rotate the second jaw towards the folded position.

11. The loading unit according to claim 9, wherein the clamping mechanism includes a cable tensioner, a first portion of the clamping cable passing from the clamping rod, through the cable tensioner, and into the end effector, the cable tensioner biased proximally to apply tension to the first portion of the clamping cable.

12. The loading unit according to claim 9, wherein the end effector includes an idler pulley, a proximal pulley, and a distal pulley rotatably attached to a lower surface of the end effector, the idler pulley positioned adjacent a proximal end of the end effector, the distal pulley positioned adjacent a distal end of the end effector, the proximal pulley positioned between the idler pulley and the distal pulley.

13. The loading unit according to claim 12, wherein each of the proximal and distal portions of the first jaw of the end effector defines a groove adjacent the central portion, and wherein a second portion of the clamping cable passes around the idler pulley, the proximal pulley, the distal pulley, and into the groove defined in the distal portion of the first jaw, the second portion of the clamping cable coupled to the second jaw.

14. The loading unit according to claim 7, wherein a distal end of the fire rod is coupled to a firing cable which is coupled to a sled disposed within the first jaw, the sled slidable through the first jaw to eject the plurality of fasteners from the first jaw.

15. The loading unit according to claim 14, wherein the sled is proximally slidable parallel to the end effector axis to eject the plurality of fasteners from the first jaw.

16. The loading unit according to claim 15, wherein distal translation of the fire rod slides the sled proximally.

17. The loading unit according to claim 7, further comprising an articulation mechanism including an articulation rod disposed within the housing and extending from an articulation flag positioned within the connector of the housing to a distal end that is coupled to the end effector, the articulation flag longitudinally translatable to articulate the end effector relative to the housing.

18. The loading unit according to claim 17, wherein the end effector is articulatable between a straight configuration and an articulated configuration, wherein in the straight configuration the end effector axis is articulated a first angle relative to the longitudinal axis of the housing, wherein in the articulated configuration the end effector axis is articulated a second angle relative to the longitudinal axis of the housing, the first angle different from the second angle.

19. The loading unit according to claim 18, wherein the second angle is in a range of −4° to 100°.

* * * * *